(12) United States Patent
Zhou et al.

(10) Patent No.: US 11,787,816 B2
(45) Date of Patent: Oct. 17, 2023

(54) CHLORIN COMPOUND, AND PREPARATION AND USE THEREOF

(71) Applicant: Southwest Jiaotong University, Chengdu (CN)

(72) Inventors: Xianli Zhou, Chengdu (CN); Shuai Huang, Chengdu (CN); Feng Gao, Chengdu (CN); Lin Chen, Chengdu (CN)

(73) Assignee: Southwest Jiaotong University, Chengdu (CN)

( * ) Notice: Subject to any disclaimer, the term of this patent is extended or adjusted under 35 U.S.C. 154(b) by 0 days.

(21) Appl. No.: 17/746,938

(22) Filed: May 17, 2022

(65) Prior Publication Data

US 2022/0281883 A1    Sep. 8, 2022

(30) Foreign Application Priority Data

Jun. 29, 2021 (CN) .......................... 202110730055.8
Jul. 1, 2021 (CN) .......................... 202110750783.5

(51) Int. Cl.
*C07D 487/22* (2006.01)
*C07F 1/04* (2006.01)
*C07F 1/00* (2006.01)
*A61P 35/00* (2006.01)

(52) U.S. Cl.
CPC ............ *C07D 487/22* (2013.01); *A61P 35/00* (2018.01); *C07F 1/005* (2013.01); *C07F 1/04* (2013.01)

(58) Field of Classification Search
CPC ........ C07D 487/22; A61P 35/00; C07F 1/005; C07F 1/04
USPC ........................................................ 514/410
See application file for complete search history.

(56) References Cited

U.S. PATENT DOCUMENTS 5,459,159 A    10/1995    Pandey et al.

FOREIGN PATENT DOCUMENTS

| CN | 1091976 A | 9/1994 |
|---|---|---|
| CN | 1944432 A | 4/2007 |
| CN | 104292235 A | 1/2015 |
| WO | 2018101434 A1 | 6/2018 |

OTHER PUBLICATIONS

Cancer [online], [retrieved on Jul. 6, 2007] Retrieved from the Internet, URL: http://www.nim.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*

* cited by examiner

*Primary Examiner* — Kristin A Vajda

(57) ABSTRACT

A chlorin compound, and a preparation and use thereof, related to medicine. The chlorin compound is represented by formula (I), or a salt, a stereisomer, a hydrate, a solvate or a prodrug thereof.

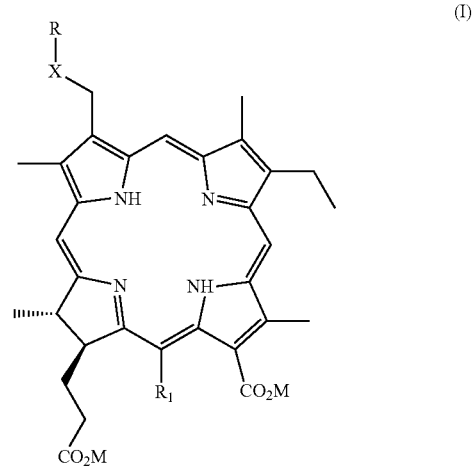

(I)

12 Claims, 3 Drawing Sheets

CHLORIN COMPOUND, AND PREPARATION AND USE THEREOF

CROSS-REFERENCE TO RELATED APPLICATIONS

This application claims the benefit of priority from Chinese Patent Application Nos. 202110750783.5 and 202110730055.8, filed on Jul. 1, 2021 and Jun. 29, 2021, respectively. The content of the aforementioned application, including any intervening amendments thereto, is incorporated herein by reference in its entirety.

TECHNICAL FIELD

This application relates to medicines, and more particularly to a chlorin compound, and a preparation and application thereof.

BACKGROUND

As one of the primary persistent ailments, cancer has attracted worldwide attention for a long term, and extensive researches have been conducted to explore a safe and reliable therapy. Photodynamic therapy (PDT) has emerged as an effective clinical treatment tool for cancers in the past 30 years. In addition to the treatment of malignant tumors, PDT also appears to be promising in the treatment of many other diseases.

The PDT is dependent on the photodynamic effect of photosensitizers, and is mainly employed in the treatment and diagnosis of malignant tumors, and some precancerous lesions and benign lesions. The two factors affecting the performance of PDT are photosensitizer and light source with a specific wavelength corresponding thereto, where the photosensitizer directly determines the therapeutic effect of PDT against tumors. In the PDT, the photosensitizer binds to tumor cells, and then reacts with molecular oxygen upon activation via light at a specific wavelength to produce singlet oxygen, which can not only kill tumor cells, but also block or destroy blood vessels in tumor tissues. Compared with traditional tumor therapies, the PDT has the following advantages: (1) selective damage to tumor tissues without damaging normal tissues; (2) synergistic effect with chemotherapy and radiotherapy; (3) visualization of the extent and infiltration degree of the tumor by means of fluorescence to help to guide and narrow the surgery scope; and (4) mild adverse effect and simple operation. As a result, PDT is considered as a promising local treatment approach with minimal invasiveness, low toxicity and no thermogenesis.

The first-generation photosensitizer is represented by the first commercially-available photosensitizer photofrin II (Netherlands in 1993), which is indicated for tumors. The photofrin II is a complex mixture of hematoporphyrin derivatives with no controllable quality standard and severe dark toxicity, which will seriously affect the life quality of patients and cause a greater psychological burden.

The second-generation photosensitizer is predominated by porphyrin derivatives, which are generally prepared from animal heme or plant chlorophyll. These compounds have well-known chemical structure, high purity, good photothermal stability and strong absorption in the red light region, and moreover, the hydrophobic partition coefficient of the photosensitizer can be adjusted via chemical modification of the porphyrin ring, which is beneficial to the absorption and accumulation of the photosensitizer in the diseased tissue. Therefore, the porphyrin derivatives are considered as an ideal photosensitizer. Benzoporphyrin derivative monoacid A (BPD-MA), developed by QLT Inc in Canada, was approved for clinical treatment of tumors and retina macular degeneration by the U.S. Food and Drug Administration (FDA) in 2000. The BPD-MA can be employed in the treatment of deeper and larger tumors in the human body with rapid concentration in the target tissue and rapid elimination in the normal tissue. Different from photofrin II (a two-day interval is required), the light activation can be performed 5 min after the administration of BPD-MA. Due to fast absorption and elimination, the photosensitization is shortened to one day, while for photofrin II, the photosensitization lasts for several weeks. Nevertheless, as a semi-synthetic product derived from natural materials, the BPD-MA has relatively complicated synthesis process, low overall yield and high synthesis cost. At the same time, its finished drug Verteporfin is also very expensive (about $1,000 for a preparation containing 15 mg of active ingredients), which greatly limits the clinical application. This drug has not yet been registered and marketed in China.

As another important class of second-generation photosensitizers, the chlorin compounds mainly includes chlorophylls and bacteriochlorins (formed from the reduction of a double bond on a pyrrole ring in the porphyrin structure). Such compounds exhibit desirable photophysical properties, wide absorption wavelength range and strong absorption at the visible region. Theoretically, these compounds are promising as drugs for PDT of tumors. As disclosed by U.S. Pat. No. 5,459,159, 2-(1-hexyloxy)ethyl-2-devinyl pyropheophorbide-a (HPPH), semi-synthesized from chlorophyll a, can absorb light further into red portion of the spectrum, and has high penetration rate into tumor tissues, low dark toxicity, high selectivity to target cells and short retention time in the skin. The phase II clinical trials for this compound have been completed in the US, and the results indicate a promising clinical application prospect. Unfortunately, HPPH is water-insoluble, and thus it is necessary to introduce ethanol and a surfactant such as Tween 80 for solubilization to prepare a water injection. However, these additives will cause toxicity and irritation, and make the preparation more complicated. In view of this, some US researchers have adopted liposomes, oils and polymeric micelles to encapsulate this compound. Nevertheless, after the controlled drug release or photosensitization, the photosensitizer will freely circulate in the body and accumulates in the eyes and skin, thereby leading to the phototoxic side effect and leaving the patients highly sensitive to light.

Chinese patent application publication No. 104292235, titled "2-(1-n-hexyloxy)ethyl chlorin f salt, pharmaceutical composition and application thereof" and published on Jan. 21, 2015, discloses that 2-(1-n-hexyloxy)ethyl chlorin f sodium salt is water-soluble and stable, thus can be used as a photosensitizer or a sonosensitizer for the treatment and diagnosis of larger malignant tumors and precancerous or benign lesions Unfortunately, the 1'-position carbon in the HPPH and 2-(1-n-hexyloxy)ethyl chlorin f sodium salt is asymmetric, and these two compounds both are racemic compounds. Considering that the drug efficacy and toxicity is closely related to the spatial configuration, and the two enantiomers are generally absorbed in different ways, different physiological activities will be generated. The configuration uncertainty will render the treatment effect uncontrollable.

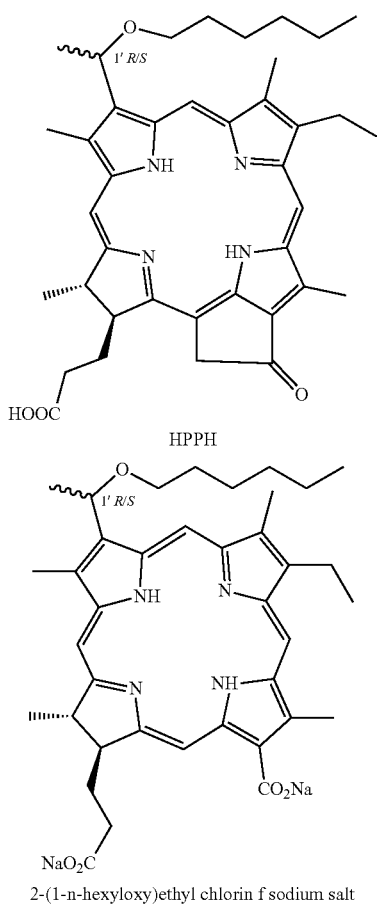

HPPH 2-(1-n-hexyloxy)ethyl chlorin f sodium salt

Sonodynamic therapy (SDT) is another emerging tumor treatment strategy, in which the low-intensity ultrasound is combined with a chemical drug (known as sonosensitizer) to generate reactive oxygen species (ROS) to produce antitumor effects. Compared with traditional anti-cancer therapy, the SDT has the advantages of non-invasiveness, strong targetability and convenient operation. Compared with PDT, SDT not only provides stronger penetration and more precise targeted drug delivery, but also reduces tissue degeneration caused by the photostimulation, and has attracted extensive attention in recent years. An appropriate sonosensitizer is vital for the therapeutic effect of SDT.

In summary, it is of great significance to develop a photosensitizer and sonosensitizer with desirable effect, low toxicity, and controllable quality.

SUMMARY

An objective of this application is to provide a chlorin compound, and a preparation and application thereof.

Technical solutions of this application are described as follows.

In a first aspect, this application provides a compound of formula (I), or a salt, a stereisomer, a hydrate, a solvate or a prodrug thereof:

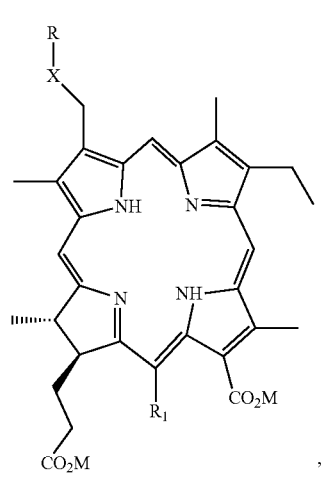

wherein R is selected from the group consisting of substituted and unsubstituted $C_{1-15}$ alkyl, substituted and unsubstituted $C_{2-15}$ alkenyl, substituted and unsubstituted $C_{2-15}$ alkynyl, substituted and unsubstituted $C_{1-15}$ acyl, substituted and unsubstituted 3-8 membered cycloalkyl, substituted and unsubstituted 5-10 membered heteroaryl, substituted and unsubstituted 5-15 membered heteroaralkyl, substituted and unsubstituted 6-15 membered aralkyl and substituted and unsubstituted 6-14 aryl; wherein the substituted $C_{1-15}$ alkyl, substituted $C_{2-15}$ alkenyl, substituted $C_{2-15}$ alkynyl, substituted $C_{1-15}$ acyl, substituted 3-8 membered cycloalkyl, substituted 5-10 membered heteroaryl, substituted 5-15 membered heteroaralkyl, substituted 6-15 membered aralkyl and substituted 6-14 aryl comprises one or more substituents independently selected from the group consisting of halogen, hydroxyl, amino, sulfhydryl, 3-8 membered cycloalkyl, 5-8 membered heteroaryl, 6-10 aryl, $C_{1-15}$ alkyl, $C_{2-15}$ alkenyl, $C_{2-15}$ alkynyl and $C_{1-15}$ acyl;

$R_1$ is hydrogen, methyl or carboxyl group;

X is O or NH; and

M is H, an alkali metal ion or $NH_4^+$.

In an embodiment, R is a $C_{1-12}$ alkyl;

$R_1$ is hydrogen or methyl;

X is O or NH; and

M is H, an alkali metal ion or $NH_4^+$.

In an embodiment, the compound is represented by formula (II):

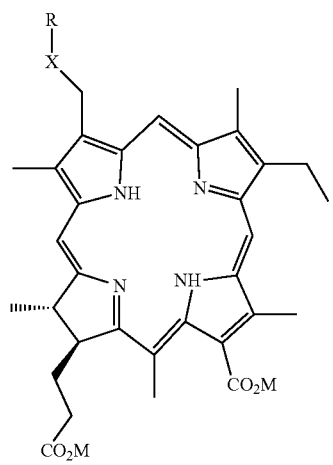

wherein R is a $C_{1-12}$ alkyl;

X is O or NH; and

M is H, an alkali metal ion or $NH_4^+$.

In an embodiment, the compound is represented by formula (II-1):

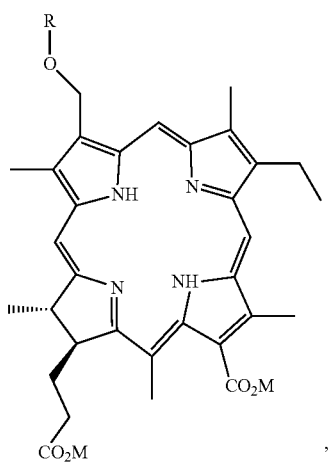
(II-1)

wherein R is a $C_{1-12}$ alkyl; and

M is H, an alkali metal ion or $NH_4^+$; or the compound is represented by formula (II-2):

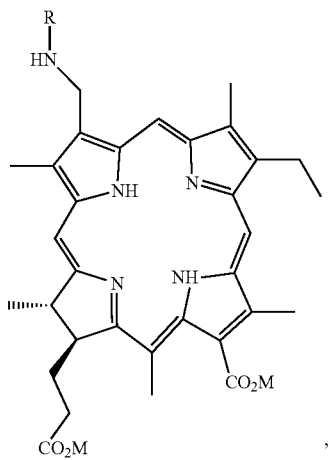
(II-2)

wherein R is a $C_{1-12}$ alkyl; and

M is H, an alkali metal ion or $NH_4^+$.

In an embodiment, the compound is represented by formula (III-1):

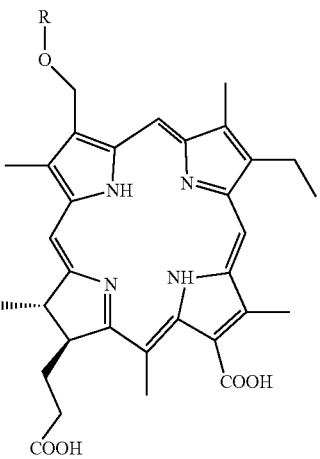
(III-1)

wherein R is a $C_{1-12}$ alkyl; or
the compound is represented by formula (III-2):

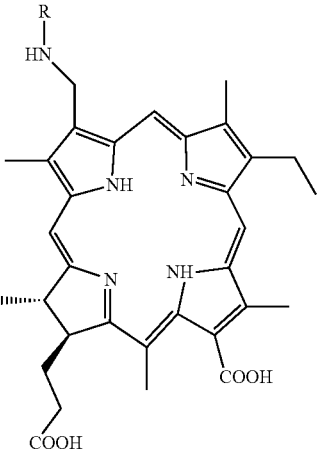
(III-2)

wherein R is a $C_{1-12}$ alkyl; or
the compound is represented by formula (III-3):

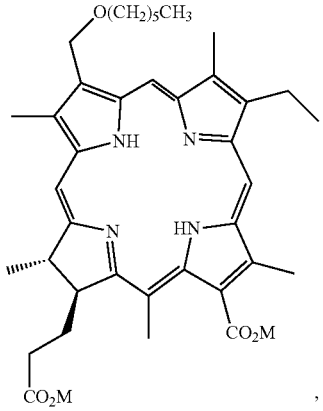
(III-3)

wherein M is H, an alkali metal ion or $NH_4^+$; or the compound is represented by formula (III-4):
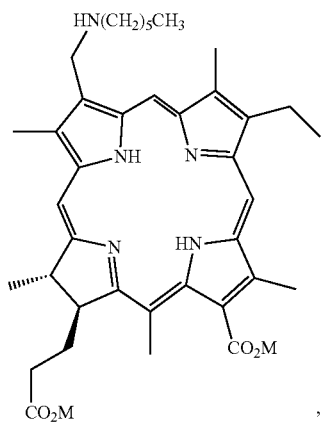
(III-4)
wherein M is H, an alkali metal ion or $NH_4^+$.
In an embodiment, the alkali metal ion is $Na^+$ or $K^+$.
In an embodiment, the compound is selected from the group consisting of:
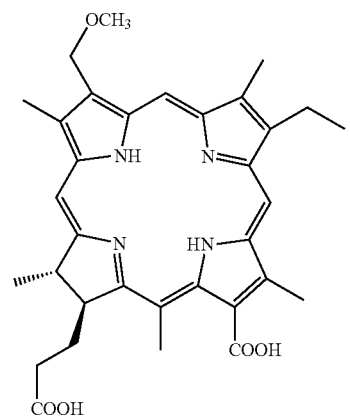
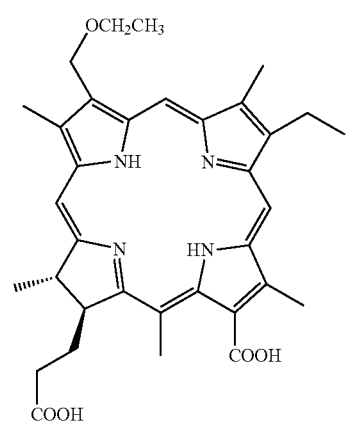
-continued
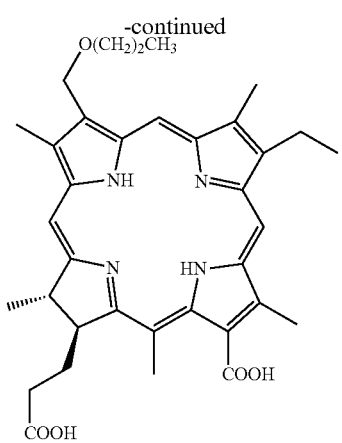
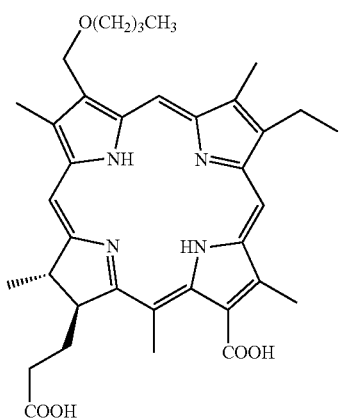
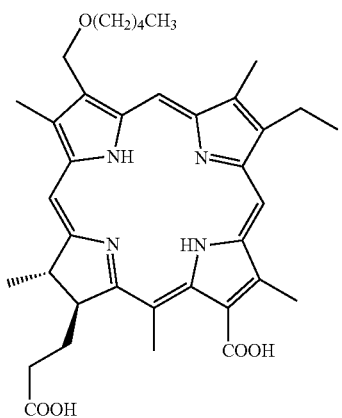
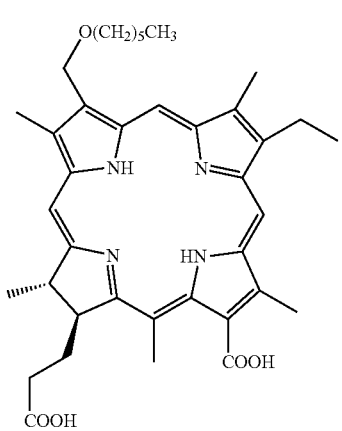

-continued
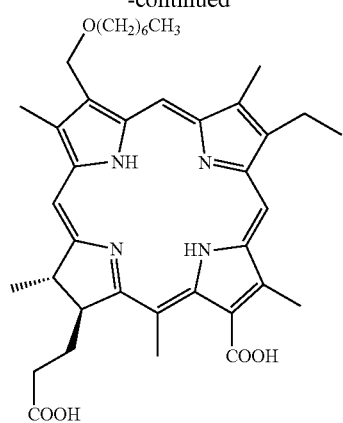
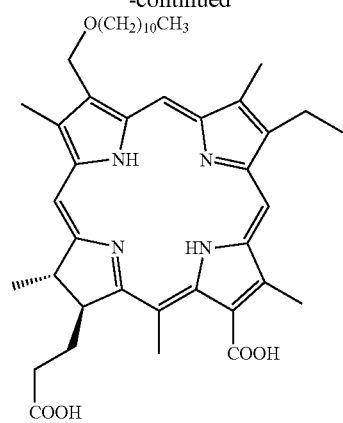
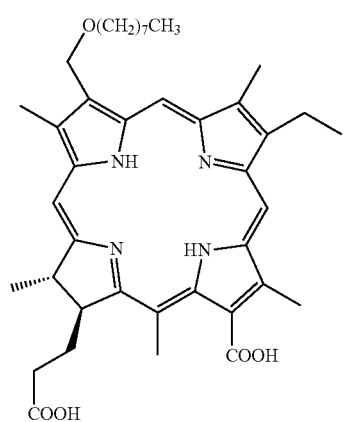
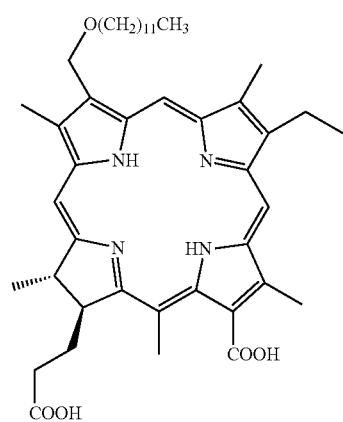
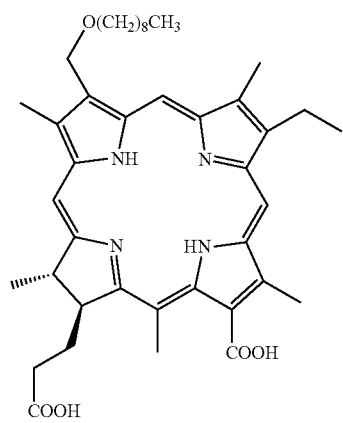
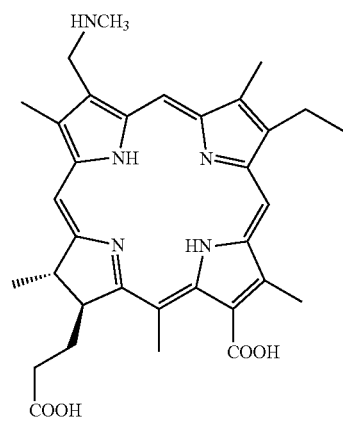
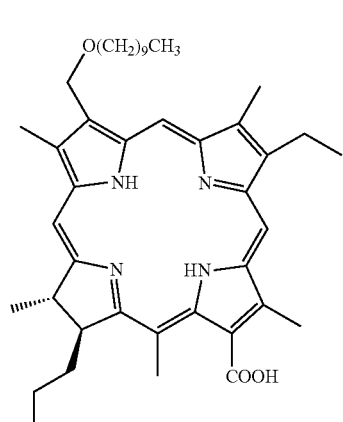
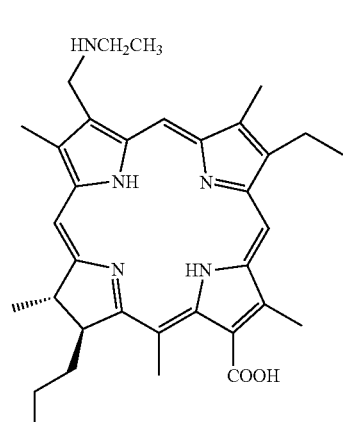

-continued
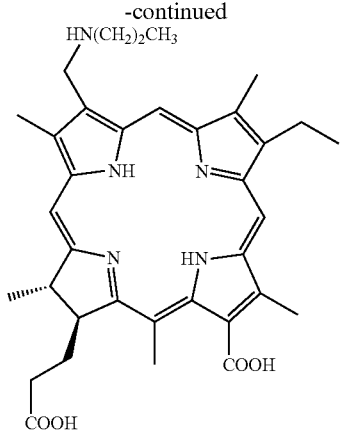
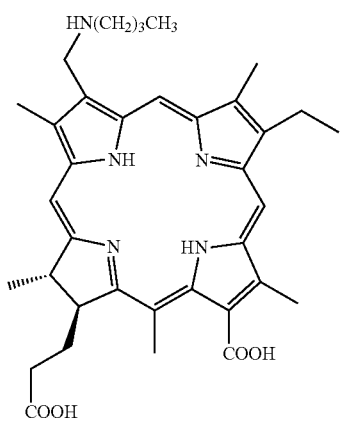
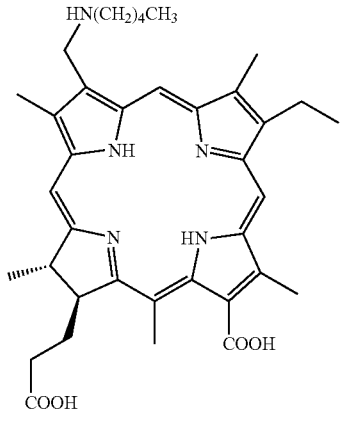
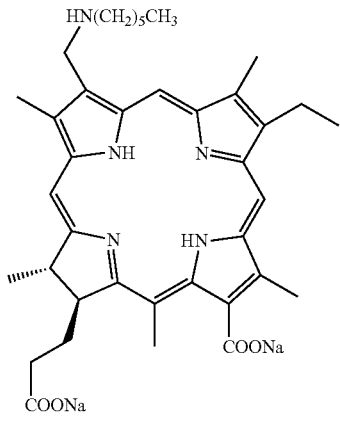
-continued
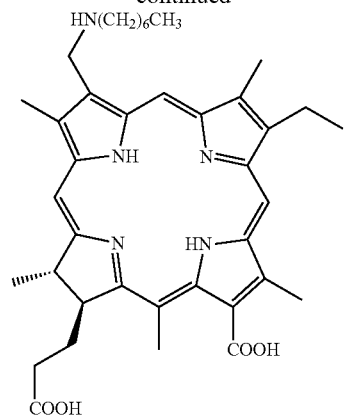
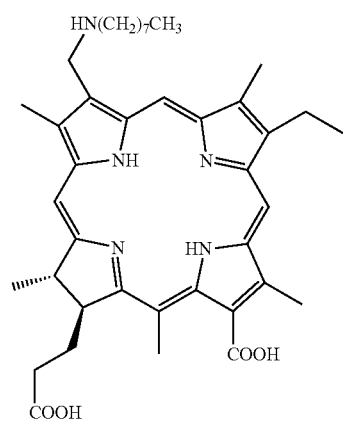
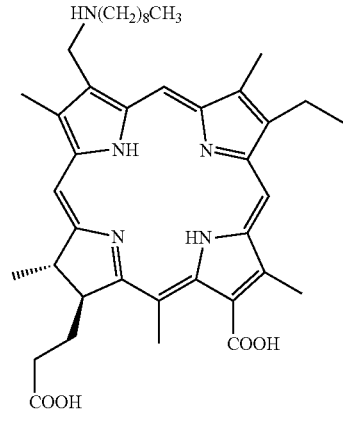
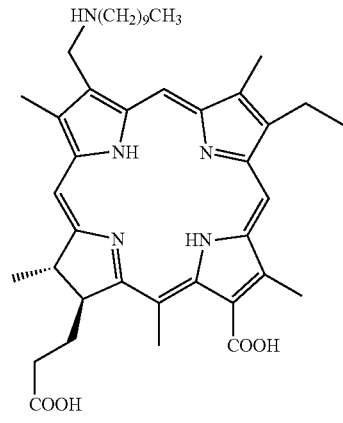

-continued
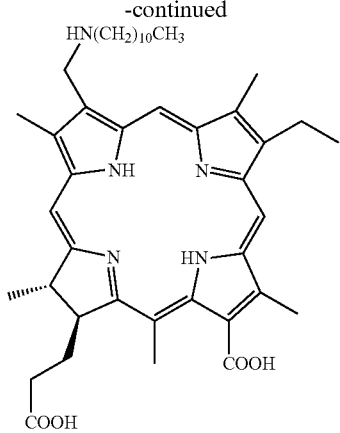
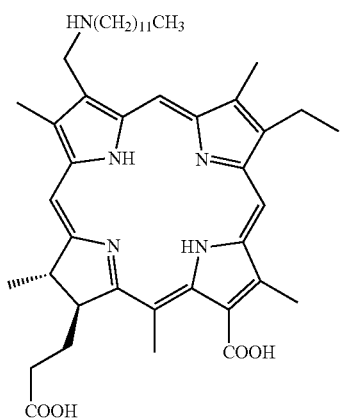
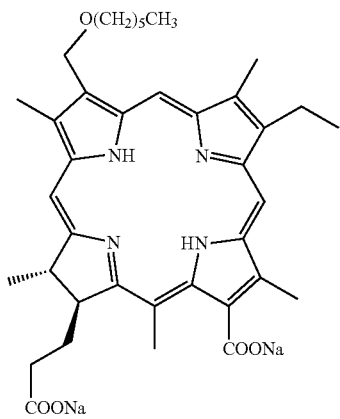
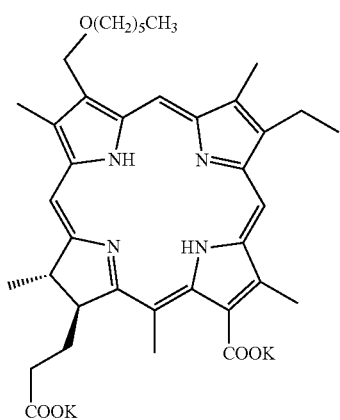
-continued
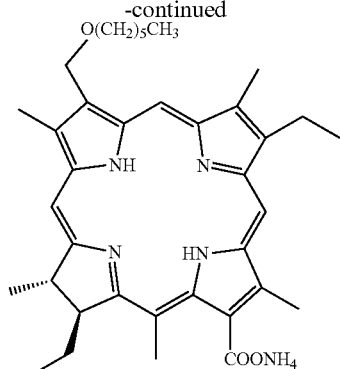
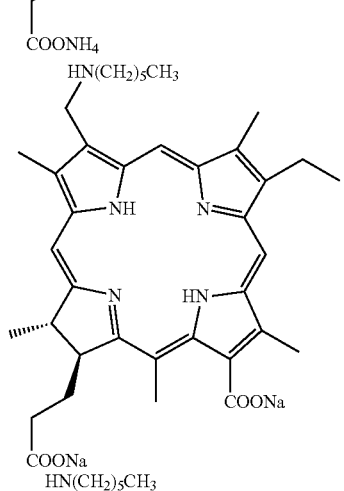
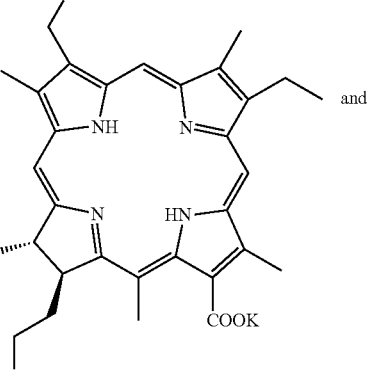
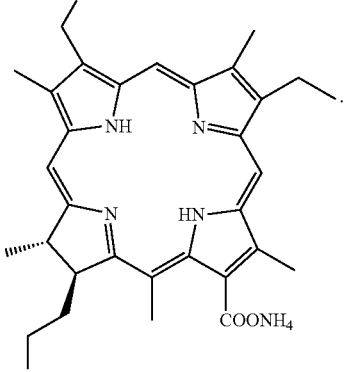
and
In a second aspect, this application provides a method for preparing the above-mentioned compound, comprising:

subjecting chlorin e4 to alkylation with (trimethylsilyl)diazomethane to produce chlorin e4 dimethyl ester; reacting the chlorin e4 dimethyl ester with NaIO$_4$ in an aqueous solution containing K$_2$OsO$_4$ and N-methylmorpholine N-oxide (NMMO) to produce 3-formyl-3-devinyl-chlorin e4 dimethyl ester; reacting the 3-formyl-3-devinyl-chlorin e4 dimethyl ester with t-BuNH$_2$BH$_3$ to produce 3-hydroxymethyl-3-devinyl-chlorin e4 dimethyl ester; reacting the 3-hydroxymethyl-3-devinyl-chlorin e4 dimethyl ester with RONa in SOCl$_2$ to produce compound (IV); subjecting the compound (IV) to reaction in the presence of LiOH in methanol under reflux followed by pH adjustment with an acid to produce compound (III-1); and reacting the compound (III-1) with an alkali metal hydroxide or ammonium hydroxide to produce compound (II-1), as shown in the following reaction route:

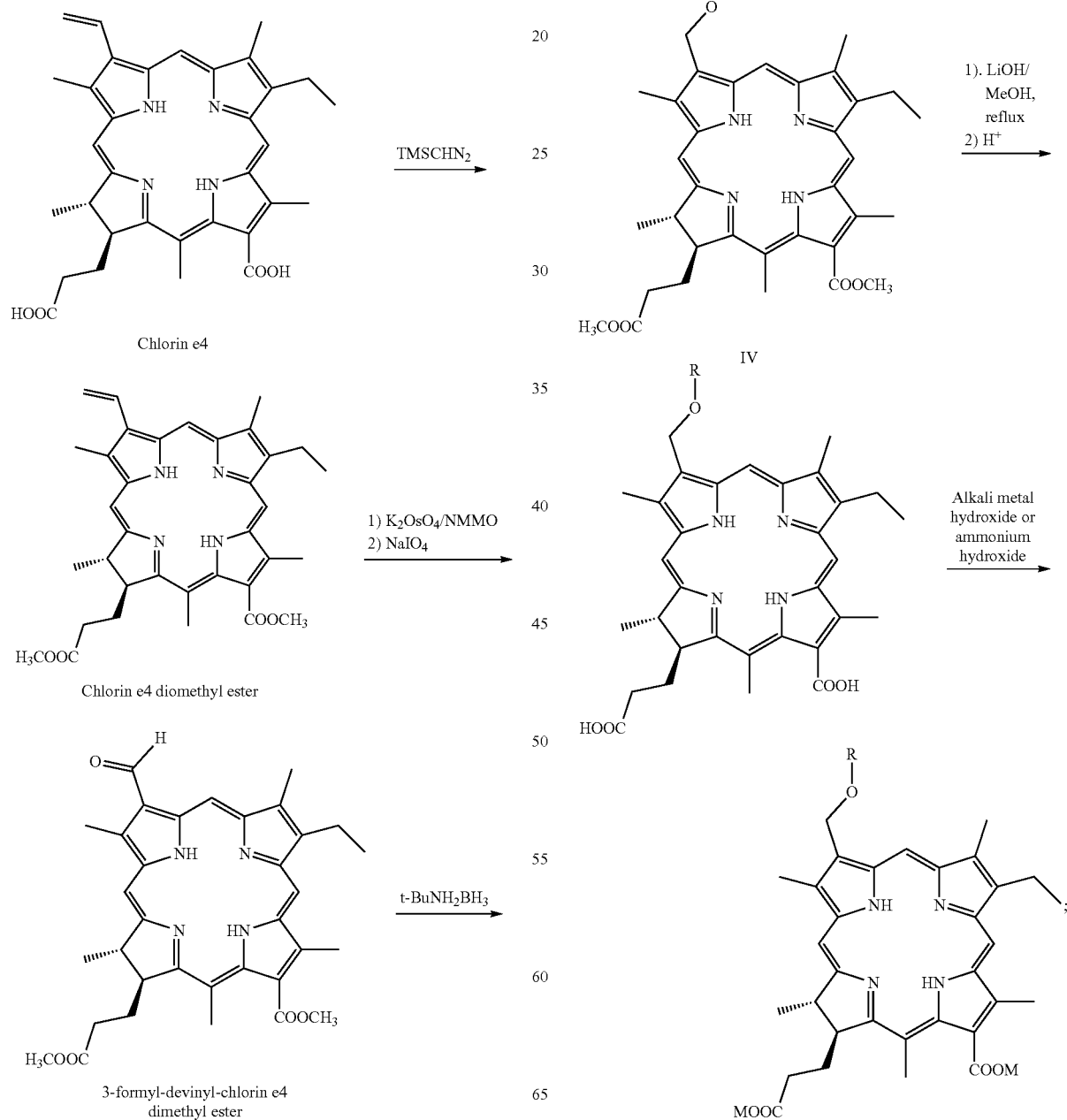

or the method comprises:

reacting chlorin e4 with NaIO$_4$ in an aqueous solution containing K2OsO4 and NMMO to produce 3-formyl-3-devinyl-chlorin e4; reacting the 3-formyl-3-devinyl-chlorin e4 with NH$_2$R followed by reaction with NaBH4 in an ice bath to produce compound (III-2); and reacting the compound (III-2) with an alkali metal hydroxide or ammonium hydroxide to produce compound (I1-2), as shown in the following reaction route:

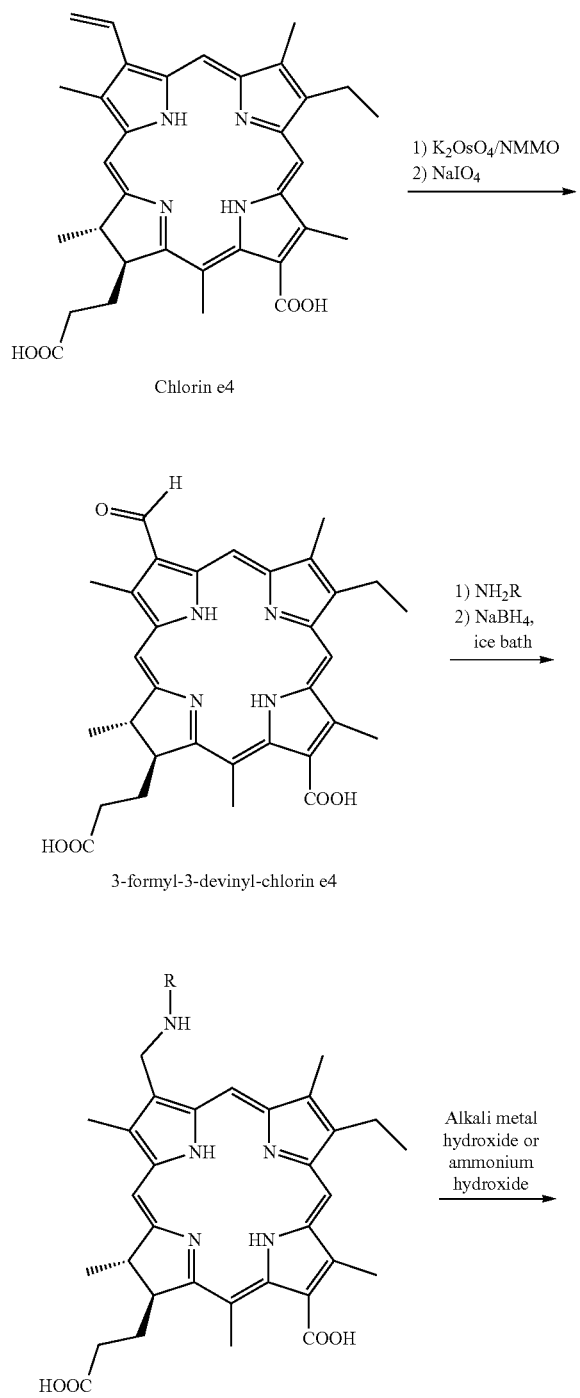

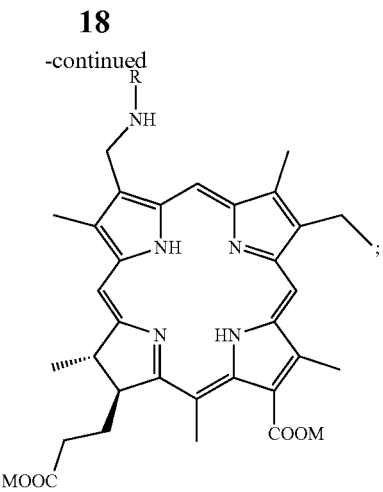

wherein R and M are defined as above.

In a third aspect, this application provides a use of the above-mentioned compound, or a salt, a stereisomer, a hydrate, a solvate or a prodrug thereof in the preparation of a drug, where the drug is a photosensitizer for photodynamic therapy or a sonosensitizer for sonodynamic therapy.

In an embodiment, the drug is used for treatment or diagnosis of a malignant tumor, a precancerous lesion, and a benign lesion;

where the malignant tumor is solid tumor; and/or the precancerous lesion is Barrett's esophagus or oral leukoplakia; and/or the benign lesion is age-related macular degeneration, atherosclerotic plaque, rheumatoid arthritis, microvascular malformation of skin, psoriasis or lupus erythematosus lesion.

In an embodiment, the solid tumor is selected from the group consisting of glioma, bladder cancer, esophageal cancer, bronchial cancer, oral and maxillofacial cancer, nasopharyngeal cancer, pleural mesothelioma, liver cancer, pancreatic cancer, skin cancer, penile cancer, cervical cancer, breast cancer and subcutaneous metastatic nodules after radical mastectomy, perianal tumor and residual cancer after extended resection of the perianal tumor, Kaposi's sarcoma, lung cancer, gastric cancer, cholangiocarcinoma, prostate cancer, melanoma and brain tumor.

In a fourth aspect, this application provides a drug, comprising:

the above-mentioned compound, or a salt, a stereisomer, a hydrate, a solvate or a prodrug thereof as an active ingredient; and a pharmaceutically acceptable excipient or auxiliary ingredient.

In a fifth aspect, this application provides a pharmaceutical composition, comprising:

the above-mentioned compound, a salt, a stereisomer, a hydrate, a solvate or a prodrug thereof; and one or more pharmaceutically acceptable excipients.

In a sixth aspect, this application provides a medicine box, comprising:

the above-mentioned compound, a salt, a stereisomer, a hydrate, a solvate or a prodrug thereof.

The above drug, pharmaceutical composition medicine box can be applied in the photodynamic therapy or sonodynamic therapy.

In a seventh aspect, this application provides a method for treating or diagnosing a malignant tumor, a precancerous lesion, or a benign lesion in a subject in need thereof, comprising:

administering to the subject an effective amount of the compound provided herein or a pharmaceutical composition thereof followed by light irradiation at a specific wavelength or ultrasound.

In one embodiment, the malignant tumor is a solid tumor, such as bladder cancer, esophageal cancer, bronchial cancer, oral and maxillofacial cancer, nasopharyngeal cancer, pleural mesothelioma, liver cancer, pancreatic cancer, skin cancer, penile cancer, cervical cancer, breast cancer and subcutaneous metastatic nodules after radical mastectomy, perianal tumor and residual cancer after extended resection of the perianal tumor, Kaposi's sarcoma, lung cancer, gastric cancer, cholangiocarcinoma, prostate cancer, melanoma and brain tumor; the precancerous lesion is Barrett's esophagus or oral leukoplakia; and the benign lesion is age-related macular degeneration, atherosclerotic plaque, rheumatoid arthritis, skin microvascular malformation, psoriasis or lupus erythematosus skin lesion.

In an embodiment, the subject is human.

In an embodiment, this application provides a medicine box comprising a solution containing the above-mentioned compound or a mixture thereof; and the compound provided herein is taken as a photosensitizer for photodynamic therapy.

In an embodiment, this application provides a medicine box comprising a lyophilized preparation of the compound or a mixture thereof; and the lyophilized preparation is dispersed in a solvent (such as water for injection and 5% glucose solution for injection) for administration in the photodynamic therapy.

The compound provided herein is both a photosensitizer and a sonosensitizer, and can be employed in the photodynamic-sonodynamic combined therapy, such that it is a potentially valuable medicine for treating malignant tumors.

Terminology

As used herein, the term "$C_{1-12}$ alkyl" refers to a branched-chain or straight-chain saturated alkyl having 1-12 carbon atoms, preferably a $C_{1-9}$ alkyl, and more preferably a $C_{5-7}$ alkyl, including but not limited to methyl, ethyl, n-propyl, isopropyl, n-butyl, sec-butyl, tert-butyl, n-pentyl, isopentyl, neopentyl, n-hexyl and n-dodecyl.

As used herein, the term "subject" refers to animals, comprising mammals and non-mammals. Mammal includes but not limited to human, non-human primates (such as chimpanzees and other apes and monkeys), farm animals (such as cows, horses, sheep, goats and pigs), domestic animals (such as rabbits, dogs and cats) and laboratory animals (including rodents, such as rats, mice, and guinea pigs). The non-mammal includes but is not limited to, birds.

As used herein, the term "effective amount" refers to an amount under which the compound provided herein can produce the desired biological or medical response.

As used herein, the term "medicine box" refers to any commercial package comprising a container for holding the compound provided herein or the pharmaceutical composition thereof, and optionally comprising a separate container such as a separate vial or a separate aluminum foil package for containing a solvent.

The container may be made of any pharmaceutically acceptable material well known in the art.

The term "treatment" as used herein comprises:

(i) prevention of diseases, namely, preventing the clinical symptoms of the disease from occurring in individuals who may suffer from this disease but have not yet felt or developed related symptoms;

(ii) inhibition of a disease, namely, inhibiting the development of the disease or clinical symptoms thereof; and (iii) alleviation or curing of a disease, namely, eliminating the disease or the clinical symptoms thereof temporarily or permanently.

As used herein, the term "pharmaceutically acceptable excipient" refers to a substance applicable to the preparation of pharmaceutical compositions, which is generally safe, non-toxic, and free of undesirable biological properties, including excipients acceptable in the veterinary medicine and human medicine.

As used herein, the term "essentially consisting of" indicates that other than the specified components, the mixture is free of other substances significantly affecting its basic characteristics. For example, it indicates that, calculated by dry weight, the components account for at least 70% w/w of the mixture, such as at least 80% w/w, at least 90% w/w, at least 95% w/w, at least 98% w/w, and at least 99% w/w.

Other terms that are not defined in detail in this specification have the same meanings as commonly known by those skilled in the art.

Dosage and Administration

The compounds provided herein can be prepared in any appropriate galenic form and can be administered by any appropriate route. The compound and the mixture provided herein can be prepared into solutions, suspensions, emulsions and lyophilized preparations for injection (e.g., intraarterial injection, intravenous injection, intramuscular injection, subcutaneous injection and intraperitoneal injection) or infusion. The compound and the mixture provided herein can also be prepared into tablets, solutions and capsules for oral administration; prepared into ointments, creams, suppositories and patches for topical application; and prepared into aerosols, sprays, and powders for inhalation. The preferred administration routes are generally injection/infusion, oral and topical administration. The injection/infusion enables the rapid distribution equilibrium of the compounds provided herein, for example, the distribution equilibrium is reached within 24 hours.

The methods for preparing the compound provided herein into the galenical form and excipients are known to those skilled in the art, for example, referring to Luo Mingsheng and Gao Tianhui "Compendium of Pharmaceutical Excipients" second edition, Sichuan Science and Technology Press. Those skilled in the art can adjust the formulation within the scope of this specification to provide various formulations for a specific administration route of without damaging the stability and therapeutic activity of the compound provided herein.

In general, the effective amount of the compound provided herein for animals, such as humans, is 0.01-10 mg/kg body weight, preferably 0.05-4 mg/kg body weight, and more preferably 0.1-2 mg/kg body weight. Whereas it should be understood that the effective amount of the compound provided herein or the mixture thereof can be determined by the researchers or clinicians based on reasonable medical judgment. The specific effective amount will depend on many factors, such as the specific disease and its severity, the specific compound, the wavelength, the light energy flow rate and the irradiation time, the age, weight, and general health status of the subject, the treatment duration, drug combination and other factors well known in the medical field. In some cases, the effective amount may be higher than the upper limit of the aforementioned range or lower than the lower limit of the aforementioned range.

When taken as a photosensitizer, the compound provided herein can be used in combination with any known excitation light source corresponding to hematoporphyrin photosensitizers in the art. In the present disclosure, the irradiation wavelength is preferably 660±5 nm, and the irradiation dose is 50-200 J/cm$^2$, preferably 75-150 J/cm$^2$.

When the compound is used as a sonosensitizer, the required dosage is 1-5 MHz and 1-5 W/cm$^2$, preferably 1-3 MHz and 2-4 W/cm$^2$.

The compound provided herein can provide desired therapeutical effect when taken as a photosensitizer in photodynamic therapy or as a sonosensitizer in sonodynamic therapy for treating the tumors, such that it can be used in the preparation of medicines for treating tumors. Moreover, it has good safety, and less toxic and side effects, and thus has promising application prospects.

Obviously, various modifications, replacements and alterations can be made by those skilled in the art without departing from the spirit of the present disclosure. It should be understood that these modifications, replacements and alterations should fall within the scope of the disclosure defined by the appended claims.

The present disclosure will be further described below with reference to the embodiments. It should be noted that the embodiments provided herein are not intended to limit the present disclosure, and technical solutions obtained based on the content disclosed herein without paying any creative effort should fall within the scope of the present disclosure.

DETAILED DESCRIPTION OF EMBODIMENTS

Figure 1A:
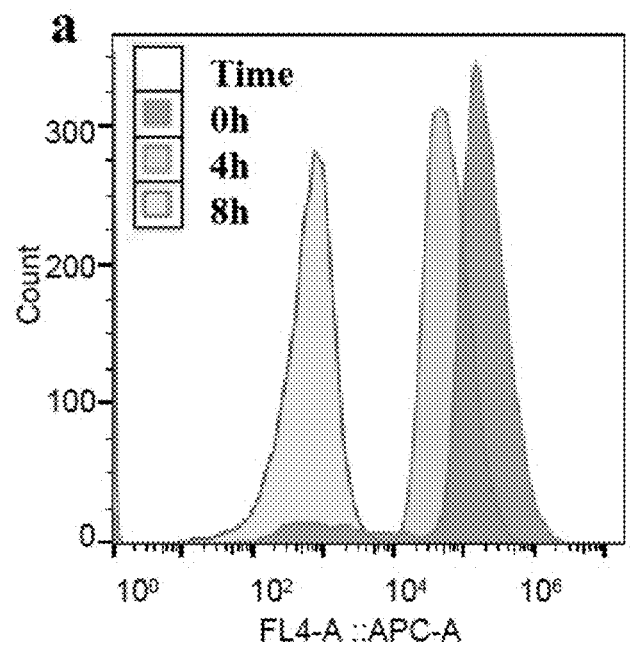
FIGS. 1a-f show flow cytometric fluorescence change results of various tumor cells treated with 3-hexyloxymethyl-3-devinyl-chlorin e4 disodium salt (CEFO) and 3-n-hexylaminomethyl-3-devinyl-chlorin e4 disodium salt (CEFN); where 1a: 4T1 cells treated with CEFO; 1b: hela cells treated with CEFO; 1c: huh-7 cells treated with CEFO; 1d: 4T1 cells treated with CEFN; 1e: hela cells treated with CEFN; and 1f: huh-7 cells treated with CEFN.

Unless otherwise specified, the raw materials and equipment used herein are all commercially available.

Example 1 Preparation of 3-hexyloxymethyl-3-devinylchlorin e4

(1) Synthesis of Chlorin e4 Dimethyl Ester 10.0 g (18.12 mmol) of chlorin e4 (CAS No. 550-52-7) was dissolved in 200 mL of a mixed solution of methanol and toluene (1:1 by volume), to which 27.3 mL of a solution of (trimethylsilyl)diazomethane (3 eq, 2 mol/L) in n-hexane was slowly added dropwise under ice bath. The reaction mixture was reacted under stirring at room temperature for 3 hours. After the reaction was confirmed by TLC to be completed, the reaction mixture was added with 0.5 mL of glacial acetic acid and stirred for 10 min to quench the reaction. Then the reaction mixture was evaporated under reduced pressure and subjected to extraction with a mixture of ethyl acetate and water (1:1, v/v). The ethyl acetate phase was collected, and concentrated under reduced pressure to obtain a crude product, which was subjected to normal phase silica gel column chromatography and petroleum ether-ethyl acetate (volume ratio from 50:1 to 1:1) gradient elution to give 9.5 g of dark green chlorin e4 dimethyl ester (90.3% yield).

HR-ESI-MS: m/z 581.3077 [M+H]$^+$ (calcd. for $C_{35}H_{40}N_4O_4$, 581.3083[M+H]+).

The chlorin e4 dimethyl ester is structurally shown as follows:

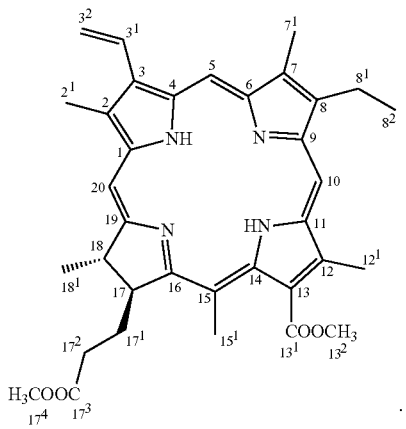

(2) Synthesis of 3-formyl-3-devinyl-chlorin e4 dimethyl ester 290 mg (0.50 mmol) of chlorin e4 dimethyl ester was dissolved in 50 mL of tetrahydrofuran, to which 10 mL of an aqueous solution containing 176 mg (3 eq) of N-Methyl-morpholine-N-oxide and 10 mg (0.05 eq) of potassium osmate was added. The reaction mixture was stirred at room temperature for 1 h, added with 10 mL of a sodium periodate aqueous solution (containing 535 mg (5 eq) of sodium periodate) and stirred in a 55° C.-water bath for 3 h. After the reaction was confirmed by TLC to be completed, the reaction mixture was added with excess sodium bisulfite and stirred for 10 min to quench the reaction. Then the reaction mixture was evaporated under reduced pressure and subjected to extraction with dichloromethane and water (1:1, v/v). The dichloromethane phase was collected, and concentrated under reduced pressure to obtain a crude product, which was subjected to normal phase silica gel column chromatography and petroleum ether-ethyl acetate (from 50:1 to 1:1, v/v) gradient elution to give 218.3 mg of reddish-brown solid 3-formyl chlorin-3-devinyl-e4 dimethyl ester (75% yield).

HR-ESI-MS: m/z 583.2881 [M+H]$^+$ (calcd. for $C_{34}H_{38}N_4O_5$, 583.2876 [M+H]$^+$). The $^1$H-NMR and $^{13}$C-NMR spectrum data of 3-formyl chlorin-3-devinyl-e4 dimethyl ester were shown in Table 1, and the chemical structure was shown as follows:

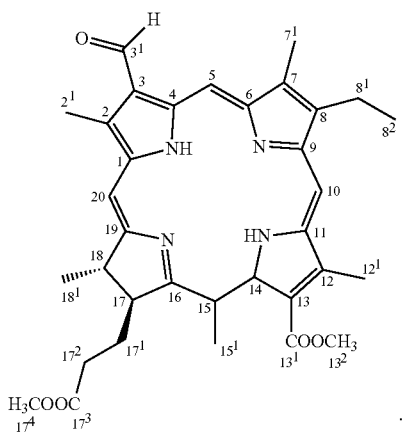

(3) Synthesis of 3-hydroxymethyl-3-devinyl-chlorin e4 dimethyl ester 117 mg (0.20 mmol) of 3-formyl-3-devinyl-chlorin e4 dimethyl ester was dissolved in 20 mL of dichloromethane, to which 86 mg (5 eq) of tert-butylamine borane was added. The reaction mixture was reacted under stirring at room temperature for 2 h. After the reaction was confirmed by TLC to be completed, the reaction mixture was added with 1 mL of 2% dilute hydrochloric acid and stirred for 10 min to quench the reaction, and subjected to extraction with dichloromethane and water (1:1, v/v). The dichloromethane phase was collected, and concentrated under reduced pressure to obtain a dark green crude product, which was subjected to normal phase silica gel column chromatography and petroleum ether-ethyl acetate (from 50:1 to 1:1, v/v) gradient elution to obtain 83 mg of dark green solid 3-hydroxymethyl-3-devinyl-chlorin e4 dimethyl ester (71% yield).

HR-ESI-MS: m/z 585.3039 [M+H]$^+$ (calcd. for $C_{34}H_{40}N_4O_5$, 585.3032[M+H]$^+$). The $^1$H-NMR (400 MHz, CDCl$_3$) and $^{13}$C-NMR (100 MHz, CDCl$_3$) data of 3-hydroxymethyl-3-devinyl-chlorin e4 dimethyl ester were shown in Table 1, and the chemical structure was shown as follows:

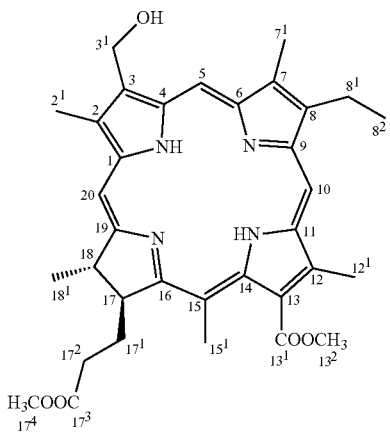

TABLE 1

NMR data of 3-formyl-3-devinyl-chlorin e4 dimethyl ester and 3-hydroxymethyl-3-devinyl-chlorin e4 dimethyl ester

| Position | 3-formyl-3-divinyl-chlorin e4 dimethyl ester | | 3-hydroxymethyl-3-devinyl-chlorin e4 dimethyl ester | |
|---|---|---|---|---|
| | $\delta_C$ | $\delta_H$ (J = Hz) | $\delta_C$ | $\delta_H$ (J = Hz) |
| 1 | 138.0 s | | 138.8 s | |
| 2 | 131.9 s | | 132.3 s | |
| 3 | 135.6 s | | 135.2 s | |
| 4 | 134.1 s | | 135.2 s | |
| 5 | 100.1 d | 9.58(1H, s) | 97.5 d | 9.23(1H, s) |
| 6 | 155.2 s | | 154.6 s | |
| 7 | 136.3 s | | 135.4 s | |
| 8 | 144.9 s | | 144.9 s | |
| 9 | 151.5 s | | 149.0 s | |
| 10 | 100.5 d | 10.12(1H, s) | 101.5 d | 9.64(1H, s) |
| 11 | 137.8 s | | 135.9 s | |
| 12 | 128.4 s | | 129.4 s | |
| 13 | 126.4 s | | 124.4 s | |
| 14 | 137.1 s | | 135.4 s | |
| 15 | 106.8 s | | 105.7 s | |
| 16 | 167.2 s | | 165.6 s | |
| 17 | 54.1 d | 4.45-4.58(1H, m) | 53.4 d | 4.42-4.62(1H, m) |
| 18 | 48.4 d | 4.45-4.58(1H, m) | 49.0 d | 4.42-4.62(1H, m) |
| 19 | 169.9 s | | 170.3 s | |
| 20 | 95.5 d | 8.94(1H, s) | 93.6 d | 8.73(1H, s) |
| 2$^1$ | 11.5 q | 3.60(3H, s) | 11.3 q | 3.23(3H, s) |
| 3$^1$ | 188.4 d | 11.47(1H, s) | 56.2 t | 5.32-5.55(2H, m) |
| 7$^1$ | 11.3 q | 3.24(3H, s) | 11.0 q | 3.18(3H, s) |
| 8$^1$ | 19.3 t | 3.69(2H, q, J = 7.6 Hz) | 19.7 t | 3.69(2H, q, J = 7.6 Hz) |
| 8$^2$ | 17.6 q | 1.70(3H, t, J = 7.6 Hz) | 17.7 q | 1.71(3H, t, J = 7.6 Hz) |
| 12$^1$ | 12.3 q | 3.89(3H, s) | 12.2 q | 3.89(3H, s) |
| 13$^1$ | 167.9 s | | 169.0 s | |
| 13$^2$ | 53.2 q | 4.35(3H, s) | 53.0 q | 4.36(3H, s) |
| 15$^1$ | 20.0 q | 3.75(3H, s) | 20.1 q | 3.64(3H, s) |
| 17$^1$ | 31.3 t | 2.37-2.72(2H, m) | 31.2 t | 2.44-2.71(2H, m) |
| 17$^2$ | 29.8 t | 1.90-2.37(2H, m) | 30.0 t | 1.96-2.31(2H, m) |
| 17$^3$ | 173.8 s | | 173.9 s | |
| 17$^4$ | 51.7 q | 3.66(3H, s) | 51.7 q | 3.60(3H, s) |
| 18$^1$ | 23.9 q | 1.79(3H, d, J = 7.2 Hz) | 23.6 q | 1.81(3H, d, J = 7.2 Hz) |

(4) Synthesis of 3-hexyloxymethyl-3-devinyl-chlorin e4

34 mg (0.40 mmol) of 3-hydroxymethyl-3-devinyl-chlorin e4 dimethyl ester was dissolved in 40 mL of anhydrous dichloromethane, to which 45 μL of (1.5 eq) thionyl chloride was added. The reaction mixture was stirred at room temperature for 30 min, added with a slight excess of a sodium n-hexanoxide solution and reacted under stirring for 10 min, where the sodium n-hexanoxide solution was prepared by adding a slight excess of sodium metal particle to a hexanol-diethyl ether mixed solution (volume ratio=1:1) and stirring at room temperature until no obvious bubbles were generated. After the reaction was confirmed by TLC to be completed, the reaction mixture was added with 1 mL of 2% dilute hydrochloric acid and stirred for 10 min to quench the reaction, and then subjected to extraction with dichloromethane and water (1:1, v/v). The dichloromethane phase was collected, and concentrated under reduced pressure to obtain a crude product a, which was dissolved in 30 mL of methanol, added with 20 mL of a 25% lithium hydroxide aqueous solution, and refluxed and stirred at 80° C. for 3 h. After the reaction was confirmed by TLC to be completed, the reaction mixture was added with 5 times the amount of water, adjusted to pH 5-6 with 2 mol/L dilute hydrochloric acid and subjected to vacuum filtration to obtain a crude product b. The crude product b was subjected to normal phase silica gel column chromatography, dichloromethane-methanol-glacial acetic acid (volume ratio from 100:1:0.2 to 5:1:0.2) gradient elution and thin layer chromatography. The eluates were combined to obtain a total of 144.6 mg of dark green solid 3-hexyloxymethyl-3-devinyl-chlorin e4 (56.5% yield).

HR-ESI-MS: m/z 641.3664 [M+H]$^+$ (calcd. for $C_{38}H_{48}N_4O_5$, 641.3658[M+H]$^+$).

The $^1$H-NMR (400 MHz, DMSO-d$_6$) and $^{13}$C-NMR (100 MHz, DMSO-d$_6$) data of 3-hexyloxymethyl-3-devinyl-chlorin e4 were shown in Table 2, and the chemical structure is shown as follows:

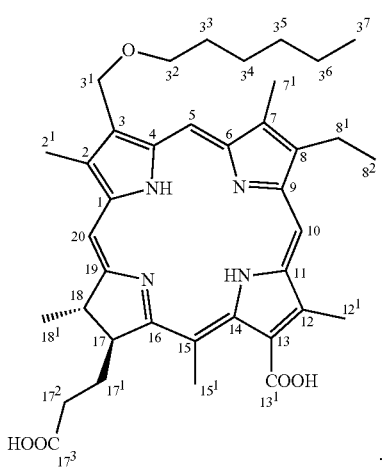 [SMILES: CCCCCCOCc1c(C)c2cc3nc(c(C)c4[nH]c(cc5nc(cc1[nH]2)C(C)=C5CC)c(C)c4C(=O)O)[C@@H](CCC(=O)O)[C@@H]3C]

TABLE 2

NMR data of 3-hexyloxymethyl-3-devinyl-chlorin e4

| Position | $\delta_C$ | $\delta_H$ (J = Hz) | Position | $\delta_C$ | $\delta_H$ (J = Hz) |
|---|---|---|---|---|---|
| 1 | 137.6 s | | 20 | 93.8 d | 8.97(1H, s) |
| 2 | 132.7 s | | $2^1$ | | 10.8 q  3.29(3H, s) |
| 3 | 133.8 s | | $3^1$ | | 69.7 t  5.37(3H, s) |
| 4 | 133.6 s | | $7^1$ | | 10.7 q  3.17(3H, s) |
| 5 | 97.8 d | 9.47(1H, s) | $8^1$ | | 18.9 t  3.69(2H, q, J = 7.6 Hz) |
| 6 | 153.3 s | | $8^2$ | | 17.7 q  1.61(3H, t, J = 7.6 Hz) |
| 7 | 134.1 s | | $12^1$ | | 11.7 q  3.89(3H, s) |
| 8 | 144.4 s | | $13^1$ | | 169.3 s |
| 9 | 148.2 s | | $15^1$ | | 19.3 q  3.56(3H, s) |
| 10 | 101.7 d | 9.67(1H, s) | $17^1$ | | 31.0 t  2.49-2.68(2H, m) |
| 11 | 135.6 s | | $17^2$ | | 29.3 t  2.18-2.41(2H, m) |
| 12 | 128.8 s | | $17^3$ | | 174.3 s |
| 13 | 127.4 s | | $18^1$ | | 23.4 q  1.69(3H, d, J = 7.2 Hz) |
| 14 | 134.8 s | | $3^2$-OC$_6$H$_{13}$ | | 63.1 t  3.56(2H, m) |
| 15 | 105.3 s | | | | 29.8 t  1.51(2H, m) |
| 16 | 166.2 s | | | | 28.9 t |
| 17 | 52.9 d | 4.53(1H, m) | | | 25.5 t  0.99-1.15(6H, m) |
| 18 | 47.8 d | 4.53(1H, m) | | | 23.0 t |
| 19 | 170.6 s | | | | 13.7 q  0.67(3H, m) |

Example 2 Preparation of 3-hexoxymethyl-3-devinyl-chlorin e4 disodium salt 160 mg (0.25 mmol) of 3-hexyloxymethyl-3-devinyl-chlorin e4 was dissolved in 100 mL of an acetone-methanol (20:1 by volume) mixed solution, to which a slight excess of a 1 mol/L sodium hydroxide-methanol solution was added dropwise. After complete precipitation, the reaction mixture was subjected to vacuum filtration to obtain dark green solid 3-hexoxymethyl-3-devinyl-chlorin e4 disodium salt (CEFO) with a purity (determined by HPLC) of 99.86%, which was structurally shown as follows:

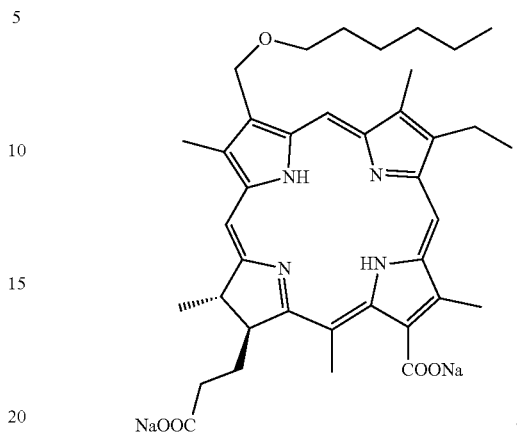

Example 3 Preparation of 3-hexyloxymethyl-3-devinyl-chlorin e4 dipotassium salt The preparation of 3-hexyloxymethyl-3-devinyl-chlorin e4 dipotassium salt was basically the same as that of Example 2 except that the sodium hydroxide in Example 2 was replaced with potassium hydroxide.

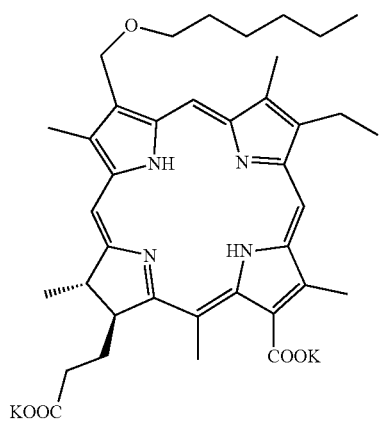

Example 4 Preparation of 3-hexyloxymethyl-3-devinyl-chlorin e4 diammonium salt The preparation of 3-hexyloxymethyl-3-devinyl-chlorin e4 diammonium salt was basically the same as that of Example 2 except that the sodium hydroxide in Example 2 was replaced with aqueous ammonia.

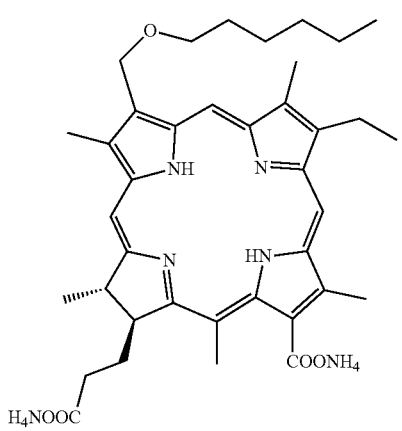

Examples 5-15

The preparations in Examples 5-15 were basically the same as that in Example 1 except that in step (4), the sodium n-hexylate was replaced with R—ONa to prepare the following compounds, where the definition of R, the specific compounds and the characterization data of the specific compounds were shown in Table 3.

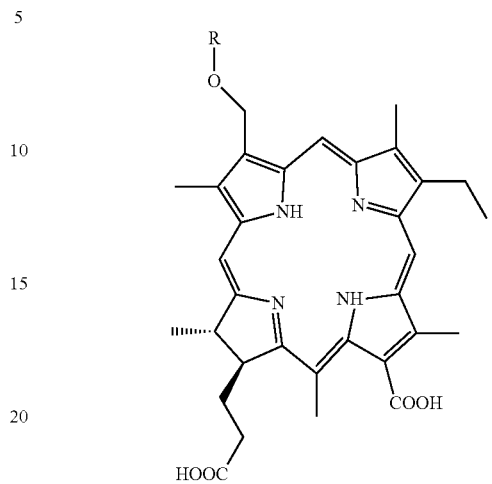

TABLE 3

| | | Structures of compounds in Examples 5-15 | |
|---|---|---|---|
| Example | R | Structural formula | ESI MS m/z [M + H]+ |
| 5 | —(CH$_2$)$_{11}$CH$_3$ | O(CH$_2$)$_{11}$CH$_3$ structure | 725.5 |
| 6 | —(CH$_2$)$_{10}$CH$_3$ | O(CH$_2$)$_{10}$CH$_3$ structure | 711.4 |

TABLE 3-continued

Structures of compounds in Examples 5-15

| Example | R | Structural formula | ESI MS m/z [M + H]+ |
|---|---|---|---|
| 7 | —(CH$_2$)$_9$CH$_3$ | | 697.6 |
| 8 | —(CH$_2$)$_8$CH$_3$ | | 683.3 |
| 9 | —(CH$_2$)$_7$CH$_3$ | | 669.6 |

TABLE 3-continued

Structures of compounds in Examples 5-15

| Example | R | Structural formula | ESI MS m/z [M + H]+ |
|---------|---|--------------------|----------------------|
| 10 | —(CH₂)₆CH₃ | | 655.7 |
| 11 | —(CH₂)₄CH₃ | | 627.7 |
| 12 | —(CH₂)₃CH₃ | | 613.8 |

TABLE 3-continued

Structures of compounds in Examples 5-15

| Example | R | Structural formula | ESI MS m/z [M + H]+ |
|---|---|---|---|
| 13 | —(CH$_2$)$_2$CH$_3$ | (structure with O(CH$_2$)$_2$CH$_3$) | 599.5 |
| 14 | —CH$_2$CH$_3$ | (structure with OCH$_2$CH$_3$) | 585.3 |
| 15 | —CH$_3$ | (structure with OCH$_3$) | 571.2 |

Example 16 Preparation of 3-n-hexylaminomethyl-3-devinyl-chlorin e4

(1) Synthesis of 3-formyl-3-devinyl-chlorin e4

276 mg (0.5 mmol) of chlorin e4 (CAS No. 550-52-7) was dissolved in 50 mL of tetrahydrofuran, to which 10 mL of an aqueous solution containing 176 mg (3 eq) of N-Methyl-morpholine-N-oxide and 10 mg (0.05 eq) of potassium osmate was added. The reaction mixture was stirred at room temperature for 1 h, added with 10 mL of a sodium periodate aqueous solution (containing 535 mg (5 eq) of sodium periodate) and stirred in a water bath at 55° C. for 3 h. After the reaction was confirmed by TLC to be completed, the reaction mixture was added with excess sodium bisulfite and stirred for 10 min to quench the reaction, and evaporated under reduced pressure and subjected to extraction with dichloromethane and water (1:1, v/v). The dichloromethane phase was collected, and concentrated under reduced pressure to obtain a crude product, which was subjected to normal-phase silica gel column chromatography and dichloromethane-methanol-glacial acetic acid (from 100:1:0.2 to 5:1:0.2, v/v/v) gradient elution to obtain a total of 160.1 mg reddish-brown solid 3-formyl-3-devinyl-chlorin e4 (57.8% yield).

HR-ESI-MS: m/z 555.2558 [M+H]$^+$ (calcd. for $C_{32}H_{34}N_4O_5$, 555.2563 [M+H]$^+$).

The $^1$H-NMR (400 MHz, DMSO-d$_6$) and $^{13}$C-NMR (100 MHz, DMSO-d$_6$) spectral data of 3-formyl-3-devinyl-chlorin e4 were shown in Table 4, and the chemical structure was shown as follows:

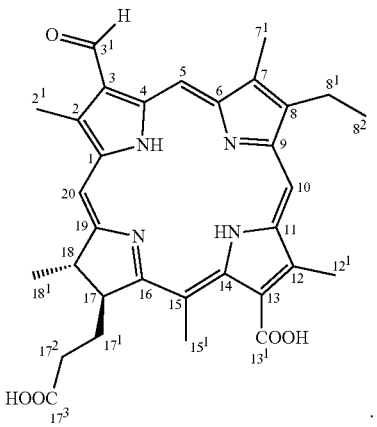 [SMILES: CCC1=C(C)c2cc3[nH]c(cc4nc(c(C)c5[nH]c(cc1n2)c(C)c5C(=O)O)[C@@H](CCC(=O)O)[C@@H]4C)c(C)c3C=O]

with 2 mL of 2% dilute hydrochloric acid and stirred for 10 min to quench the reaction. Then the reaction mixture was added with 5 times the amount of water, adjusted to pH to be near neutral with 2 mol/L sodium hydroxide and 2% dilute hydrochloric acid and subjected to vacuum filtration to obtain a crude product, which was subjected to normal phase silica gel column chromatography and dichloromethane-methanol-glacial acetic acid (from 100:1:0.2 to 5:1:0.2 by volume, v/v/v) gradient elution to give 173 mg of dark green solid 3-n-hexylaminomethyl-3-devinyl-chlorin e4 (yield of 67.6%).

HR-ESI-MS: m/z 640.3823[M+H]$^+$ (calcd. for $C_{38}H_{49}N_5O_4$, 640.3818 [M+H]$^+$). The $^1$H-NMR (400 MHz, DMSO-d$_6$) and $^{13}$C-NMR (100 MHz, DMSO-d$_6$) spectral data of 3-n-hexylaminomethyl-3-devinyl-chlorin e4 are shown in Table 5, and the chemical structure was shown as follows.

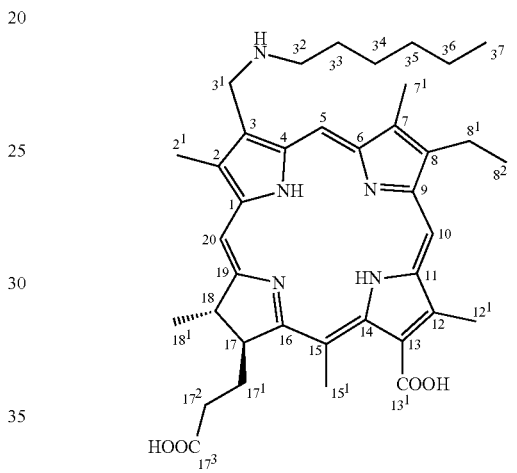

TABLE 4

$^1$H-NMR and $^{13}$C-NMR data of 3-formyl-3-devinyl-chlorin e4

| Position | $\delta_C$ | $\delta_H$ (J = Hz) | Position | $\delta_C$ | $\delta_H$ (J = Hz) |
|---|---|---|---|---|---|
| 1 | 137.8 s | | 17 | 53.5 d | 4.57-4.78(1H, m) |
| 2 | 131.3 s | | 18 | 47.3 d | 4.57-4.78(1H, m) |
| 3 | 134.8 s | | 19 | 172.0 s | |
| 4 | 132.9 s | | 20 | 95.8 d | 9.28(1H, s) |
| 5 | 99.3 d | 9.58(1H, s) | 2$^1$ | 10.9 q | 3.67(3H, s) |
| 6 | 153.6 s | | 3$^1$ | 189.3 d | 11.44(1H, s) |
| 7 | 135.1 s | | 7$^1$ | 10.6 q | 3.10(3H, s) |
| 8 | 144.2 s | | 8$^1$ | 18.3 t | 3.58(2H, q, J = 7.6 Hz) |
| 9 | 150.4 s | | 8$^2$ | 17.4 q | 1.65(3H, t, J = 7.6 Hz) |
| 10 | 99.4 d | 9.98(1H, s) | 12$^1$ | 11.7 q | 4.04(3H, s) |
| 11 | 136.9 s | | 13$^1$ | 168.6 s | |
| 12 | 129.1 s | | 15$^1$ | 21.1 q | 3.79(3H, s) |
| 13 | 127.8 s | | 17$^1$ | 31.0 t | 2.49-2.85(2H, m) |
| 14 | 135.3 s | | 17$^2$ | 29.7 t | 2.23-2.55(2H, m) |
| 15 | 106.6 s | | 17$^3$ | 174.3 s | |
| 16 | 167.7 s | | 18$^1$ | 23.6 q | 1.83(3H, d, J = 7.2 Hz) |

(2) Synthesis of 3-n-hexylaminomethyl-3-devinyl-chlorin e4

222 mg (0.40 mmol) of 3-formyl-3-devinyl-chlorin e4 was dissolved in 50 mL of methanol, to which 80 μL (1.5 eq) of n-hexylamine was added. The reaction mixture was stirred at room temperature for 1 h. After the reaction was confirmed by TLC to be completed, the reaction mixture was added with 31 mg (2 eq) of sodium borohydride and stirred for 30 min under ice bath. After the reaction was confirmed by TLC to be completed, the reaction mixture was added

TABLE 5

$^1$H-NMR and $^{13}$C-NMR data of 3-n-hexylaminomethyl-3-devinyl-chlorin e4

| Position | $\delta_C$ | $\delta_H$ (J = Hz) | Position | $\delta_C$ | $\delta_H$ (J = Hz) |
|---|---|---|---|---|---|
| 1 | 136.4 s | | 20 | 93.9 d | 9.09(1H, s) |
| 2 | 130.8 s | | 2$^1$ | 11.4 q | 3.34(3H, s) |
| 3 | 133.2 s | | 3$^1$ | 47.5 t | 5.34(2H, s) |
| 4 | 132.5 s | | 7$^1$ | 11.2 q | 3.17(3H, s) |
| 5 | 98.8 d | 9.68(1H, s) | 8$^1$ | 19.01 | 3.76(2H, q, J = 7.6 Hz) |
| 6 | 151.9 s | | 8$^2$ | 17.8 q | 1.64(3H,t, J = 7.6 Hz) |
| 7 | 133.3 s | | 12$^1$ | 11.8 q | 4.07(3H, s) |
| 8 | 143.6 s | | 13$^1$ | 167.7 s | |
| 9 | 148.8 s | | 15$^1$ | 19.1 q | 3.47(3H, s) |
| 10 | 99.0 d | 9.91(1H, s) | 17$^1$ | 30.9 t | 2.54-2.91(2H, m) |
| 11 | 135.9 s | | 17$^2$ | 29.0 t | 2.12-2.44(2H, m) |
| 12 | 128.0 s | | 17$^3$ | 173.4 s | |
| 13 | 122.7 s | | 18$^1$ | 23.7 q | 1.78(3H, d, J = 7.2 Hz) |
| 14 | 135.2 s | | 3$^2$-NHC$_6$H$_{13}$ | 40.8 t | 3.47(2H, m) |
| 15 | 106.7 s | | | 36.2 t | 1.64(2H, m) |
| 16 | 167.4 s | | | 26.1 t | |
| 17 | 53.6 d | 4.58(1H, m) | | 21.9 t | 1.12-1.23(6H, m) |
| 18 | 47.6 d | 4.58(1H, m) | | 21.8 t | |
| 19 | 173.3 s | | | 13.8 q | 0.78(3H, m) |

Example 17 Preparation of 3-n-hexylaminomethyl-3-devinyl-chlorin e4 disodium salt 3-n-hexylaminomethyl-3-devinyl-chlorin e4 was taken as the raw material. The preparation of 3-n-hexylaminomethyl-3-devinyl-chlorin e4 dipotassium salt was basically the same as that of Example 2. The chemical structure of the prepared 3-n-hexylaminomethyl-3-devinyl-chlorin e4 disodium salt (CEFN) was as follows:

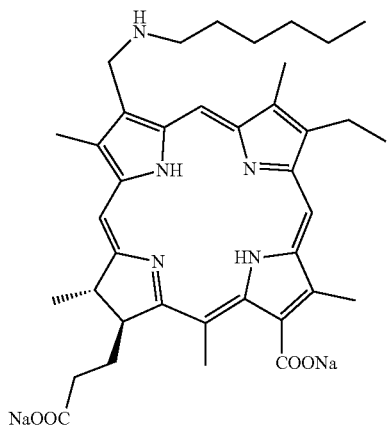

Example 18 Preparation of 3-n-hexylaminomethyl-3-devinyl-chlorin e4 dipotassium salt The preparation of 3-n-hexylaminomethyl-3-devinyl-chlorin e4 dipotassium salt was basically the same as that of Example 2 except that the sodium hydroxide in Example 2 was replaced with potassium hydroxide. The structure of the 3-n-hexylaminomethyl-3-devinyl-chlorin e4 dipotassium salt was shown as follows:

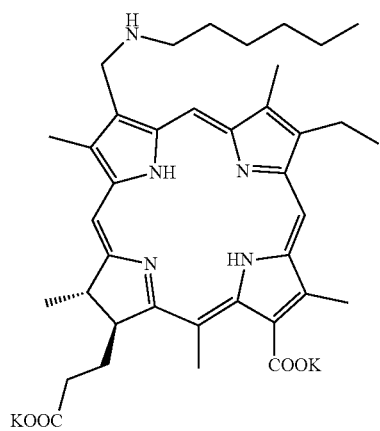

Example 19 Preparation of 3-n-hexylaminomethyl-3-devinyl-chlorin e4 diammonium salt The preparation of 3-n-hexylaminomethyl-3-devinyl-chlorin e4 diammonium salt was basically the same as that of Example 2 except that the sodium hydroxide in Example 2 was replaced with aqueous ammonia. The structure of the 3-n-hexylaminomethyl-3-devinyl-chlorin e4 diammonium salt was shown as follows:

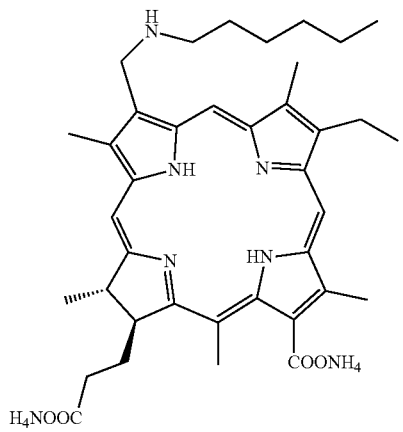

Examples 20-30

The preparations in Examples 20-30 were basically the same as that in Example 16 except that in step (2), the n-hexyl amine was replaced with R—ONa to prepare the following compounds, where the definition of R, the specific compounds and the characterization data of the specific compounds were shown in Table 6.

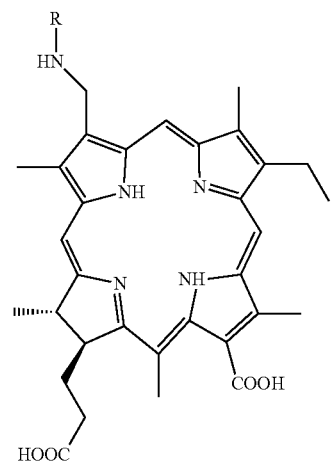

TABLE 6

Structures of compounds in Examples 20-30

| Example | R | Structural formula | ESI MS m/z [M + H]+ |
|---|---|---|---|
| 20 | —(CH$_2$)$_{11}$CH$_3$ | (structure with HN(CH$_2$)$_{11}$CH$_3$ substituent) | 724.6 |
| 21 | —(CH$_2$)$_{10}$CH$_3$ | (structure with HN(CH$_2$)$_{10}$CH$_3$ substituent) | 710.5 |
| 22 | —(CH$_2$)$_9$CH$_3$ | (structure with HN(CH$_2$)$_9$CH$_3$ substituent) | 696.6 |

TABLE 6-continued

Structures of compounds in Examples 20-30

| Example | R | Structural formula | ESI MS m/z [M + H]+ |
|---|---|---|---|
| 23 | —(CH$_2$)$_8$CH$_3$ | | 682.2 |
| 24 | —(CH$_2$)$_7$CH$_3$ | | 668.4 |
| 25 | —(CH$_2$)$_6$CH$_3$ | | 654.6 |

TABLE 6-continued

Structures of compounds in Examples 20-30

| Example | R | Structural formula | ESI MS m/z [M + H]+ |
|---|---|---|---|
| 26 | —(CH$_2$)$_4$CH$_3$ | | 626.6 |
| 27 | —(CH$_2$)$_3$CH$_3$ | | 612.4 |
| 28 | —(CH$_2$)$_2$CH$_3$ | | 598.5 |

TABLE 6-continued

Structures of compounds in Examples 20-30

| Example | R | Structural formula | ESI MS m/z [M + H]+ |
|---------|---|---|---|
| 29 | —CH₂CH₃ | (structure) | 584.6 |
| 30 | —CH₃ | (structure) | 570.7 |

The beneficial effects of the present disclosure will be demonstrated through the following experimental examples.

Experimental Example 1 Enrichment in Three Kinds of Tumor Cells

Human cervical cancer cells (Hela line), human hepatocellular carcinoma cells (huh-7 line) and murine mammary carcinoma cells (4T1 line) were harvested from the logarithmic growth phase, respectively seeded in a 6-well plate at a density of $2 \times 10^5$ cells/well and cultured at 37° C. and 5% $CO_2$ for 24 hours.

Each kind of tumor cells was co-cultured with 2 mL of 10 μg/mL CEFO (prepared in Example 2) and 2 mL of 10 μg/mL CEFN (prepared in Example 17), respectively. Samples were respectively collected at 0 h, 4 h, 8 h, 12 h, and 24 h during the incubation each for 50 μL. Each sample was added with 150 μL of PBS pre-cooled at 4° C., evenly mixed and analyzed by a flow cytometer to observe the fluorescence intensity of CEFO and CEFN in the cells, so as to indirectly reflect the CEFO and CEFN enrichment in the cells.

Figure 1B:
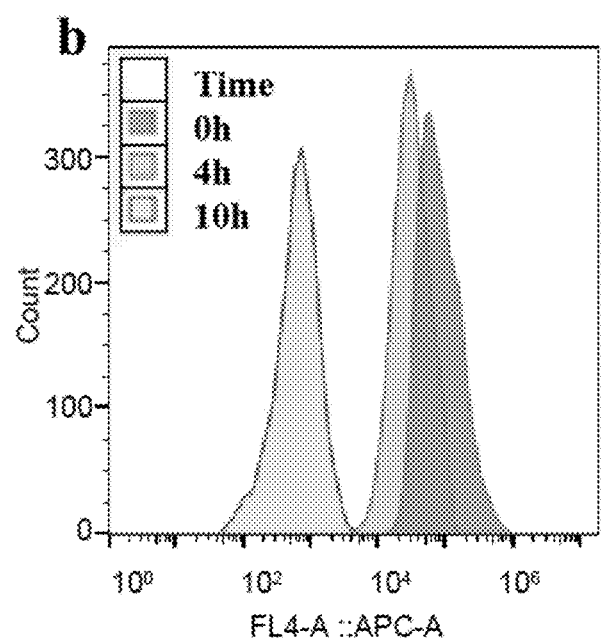
Figure 1C:
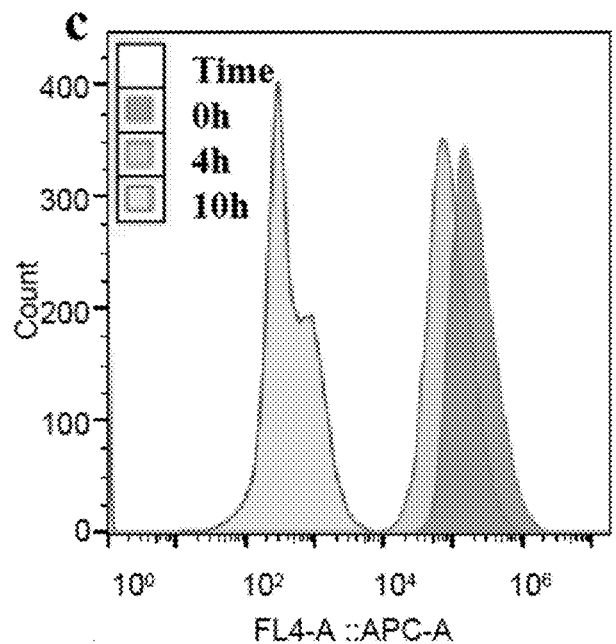
Figure 1D:
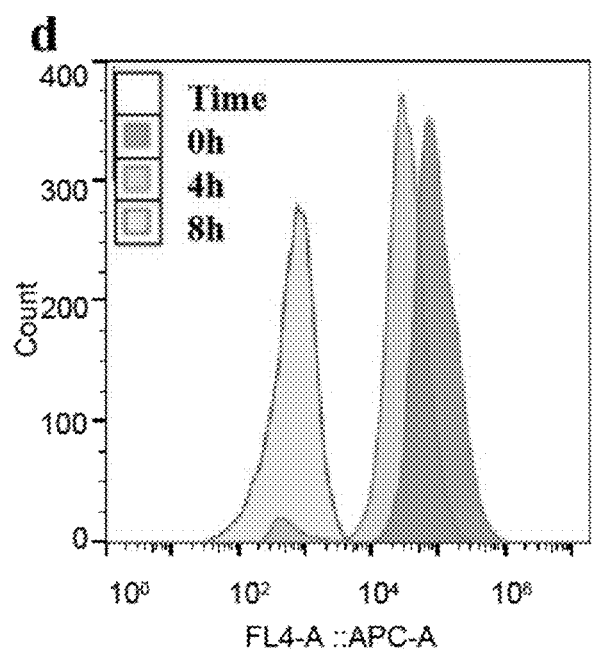
Figure 1E:
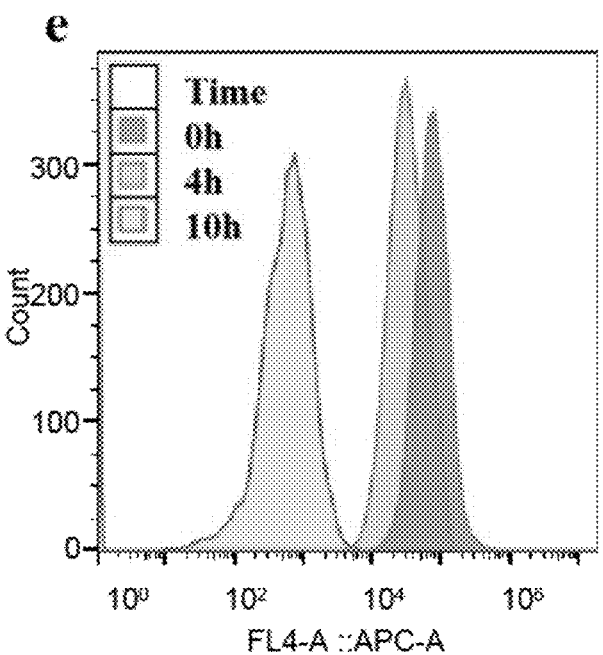
Figure 1F:
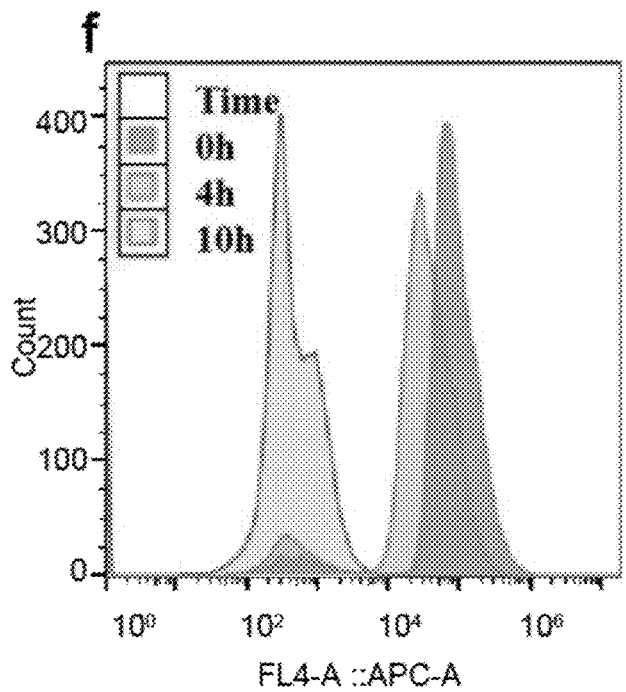

It can be demonstrated from FIGS. 1a-1f that the metabolism patterns of CEFO and CEFN in the several kinds of tumor cells were the same. In the Hela cells and huh-7 cells, the concentrations of CEFO and CEFN were basically stable after incubated for 10 h. In the 4T1 cells, the concentrations of CEFO and CEFN were basically stable after incubated for 8 h. It can be concluded that within the initial 10 hours of co-incubation, the three kinds of tumor cells all exhibited an increasing uptake of the compounds CEFO and CEFN, and the intracellular drug level was basically stable during 10-24 h of the incubation.

Experimental Example 2 Inhibitory Effect of Photosensitizer-Mediated PDT on In Vitro Proliferation of Tumor Cells Several kinds of tumor cells (human cervical cancer Hela cells, human hepatocellular carcinoma huh-7 cells and murine mammary carcinoma 4T1 cells) cultured in vitro from a variety of tissues were taken as cell models, so as to investigate the photodynamic effects mediated by different doses of CEFN, CEFO, Ce6 and HPPH on the three different tumor cells (n=3). The specific experimental procedures were carried out as follows.

Cells in the logarithmic growth phase were harvested and seeded in a 24-well plate. After growing to a confluence of 70-80%, the cells were randomly divided into a control group (free of drug and light irradiation), a drug group and a photodynamic group. The CEFN, CEFO, Ce6 and HPPH were added respectively in dark, and for each drug, four final concentrations 1, 2, 5, and 10 μg/mL were set with 3 replicates for each group. After the co-incubation, the groups were treated individually. Regarding the photodynamic group, the light irradiation was performed at a wavelength of 660 nm and three different light intensities, i.e., 2, 4 and 8 J/cm². After that, each group was digested, and were inoculated into a 96-well plate at 100 μL per well with 4 replicates for each treatment. 24 hours later, the 96-well plate was subjected to MTT assay as follows. Each well was added with 20 μL of MTT (3-4,5-dimethylthiazol-2,5-diphenyltetrazolium bromide) solution in the dark and incubated for 4 hours. The supernatant was discarded, and the residue was dissolved with 150 μL of dimethyl sulfoxide for 15 min. After that, the 96-well plate was measured by a microplate reader for the absorbance (OD value). The relative cell viability was calculated as follows: relative cell viability=OD value of experimental group/OD value of control group*100%.

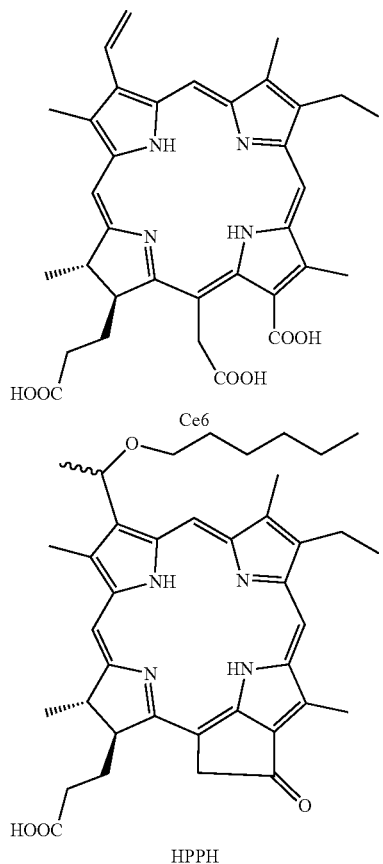

Ce6

HPPH (1) Human Cervical Cancer Hela Cell

TABLE 7

Effects of light intensity and concentration of CEFN, CEFO, Ce6 and HPPH on cell viability (%) of human cervical cancer Hela cells

|  | 1 μg/mL | 2 μg/mL | 5 μg/mL | 10 μg/mL |
|---|---|---|---|---|
| Blank group | 100 ± 3 | 104 ± 4 | 102 ± 2 | 101 ± 1 |
| CEFN | 103 ± 2 | 99 ± 2 | 106 ± 2 | 104 ± 2 |
| CEFN + 2 J/cm² | 98 ± 1 | 78 ± 3 | 43 ± 3 | 36 ± 3 |
| CEFN + 4 J/cm² | 99 ± 1 | 62 ± 2 | 32 ± 4 | 17 ± 2 |
| CEFN + 8 J/cm² | 78 ± 3 | 51 ± 3 | 21 ± 3 | 10 ± 1 |
| CEFO | 101 ± 2 | 107 ± 2 | 109 ± 2 | 107 ± 2 |
| CEFO + 2 J/cm² | 65 ± 3 | 54 ± 3 | 38 ± 2 | 25 ± 2 |
| CEFO + 4 J/cm² | 61 ± 3 | 45 ± 2 | 24 ± 3 | 4 ± 1 |

TABLE 7-continued

Effects of light intensity and concentration of CEFN, CEFO, Ce6 and HPPH on cell viability (%) of human cervical cancer Hela cells

|  | 1 μg/mL | 2 μg/mL | 5 μg/mL | 10 μg/mL |
|---|---|---|---|---|
| CEFO + 8 J/cm² | 40 ± 2 | 25 ± 2 | 14 ± 4 | 3 ± 2 |
| Ce6 | 92 ± 3 | 89 ± 2 | 86 ± 4 | 83 ± 3 |
| Ce6 + 8 J/cm² | 86 ± 3 | 76 ± 3 | 38 ± 2 | 21 ± 1 |
| HPPH | 100 ± 3 | 100 ± 2 | 102 ± 3 | 96 ± 4 |
| HPPH +8 J/cm² | 65 ± 4 | 46 ± 1 | 25 ± 2 | 12 ± 4 |

(2) Murine Mammary Carcinoma 4T1 Cells

TABLE 8

Effects of light intensity and concentration of CEFN, CEFO, Ce6 and HPPH on cell viability (%) of murine mammary carcinoma 4T1 cells

|  | 1 μg/mL | 2 μg/mL | 5 μg/mL | 10 μg/mL |
|---|---|---|---|---|
| Blank group | 102 ± 3 | 108 ± 2 | 107 ± 4 | 101 ± 2 |
| Compound CEFN | 97 ± 3 | 104 ± 1 | 98 ± 2 | 101 ± 3 |
| Compound CEFN + 2 J/cm² | 97 ± 2 | 79 ± 3 | 59 ± 2 | 38 ± 3 |
| Compound CEFN + 4 J/cm² | 89 ± 3 | 52 ± 2 | 24 ± 3 | 10 ± 2 |
| Compound CEFN + 8 J/cm² | 81 ± 3 | 39 ± 2 | 18 ± 1 | 8 ± 3 |
| Compound CEFO | 103 ± 2 | 103 ± 2 | 99 ± 2 | 100 ± 3 |
| Compound CEFO + 2 J/cm² | 86 ± 3 | 67 ± 3 | 38 ± 2 | 29 ± 1 |
| Compound CEFO + 4 J/cm² | 84 ± 4 | 41 ± 3 | 21 ± 2 | 5 ± 1 |
| Compound CEFO + 8 J/cm² | 78 ± 3 | 39 ± 2 | 19 ± 42 | 3 ± 1 |
| Ce6 | 91 ± 2 | 90 ± 3 | 86 ± 4 | 85 ± 4 |
| Ce6 + 8 J/cm² | 88 ± 2 | 79 ± 3 | 54 ± 3 | 36 ± 1 |
| HPPH | 107 ± 4 | 103 ± 2 | 98 ± 1 | 99 ± 44 |
| HPPH + 8 J/cm² | 83 ± 3 | 53 ± 2 | 33 ± 2 | 11 ± 2 |

TABLE 8a

Effect of compounds (concentration: 10 μg/mL) in different Examples on cell viability (%) of murine mammary carcinoma 4T1 cells under conditions of no light and light intensity of 8J/cm²

| Serial number | No light | +8 J/cm² |
|---|---|---|
| Example 1 | 103 ± 1 | 2 ± 5 |
| Example 5 | 100 ± 2 | 3 ± 4 |
| Example 6 | 102 ± 2 | 4 ± 3 |
| Example 7 | 102 ± 2 | 6 ± 2 |
| Example 8 | 100 ± 3 | 2 ± 3 |
| Example 9 | 101 ± 1 | 5 ± 2 |
| Example 10 | 101 ± 2 | 3 ± 2 |
| Example 11 | 104 ± 2 | 4 ± 3 |
| Example 12 | 99 ± 3 | 6 ± 4 |
| Example 13 | 102 ± 3 | 5 ± 3 |
| Example 14 | 101 ± 3 | 6 ± 1 |
| Example 15 | 100 ± 3 | 4 ± 4 |
| Example 16 | 103 ± 3 | 7 ± 5 |
| Example 20 | 104 ± 1 | 6 ± 3 |
| Example 21 | 101 ± 1 | 9 ± 2 |
| Example 22 | 99 ± 2 | 10 ± 4 |
| Example 23 | 102 ± 2 | 8 ± 5 |
| Example 24 | 100 ± 2 | 9 ± 5 |
| Example 25 | 100 ± 2 | 5 ± 3 |
| Example 26 | 102 ± 1 | 6 ± 5 |
| Example 27 | 103 ± 3 | 6 ± 2 |
| Example 28 | 104 ± 1 | 7 ± 4 |
| Example 29 | 103 ± 4 | 8 ± 2 |
| Example 30 | 102 ± 2 | 9 ± 4 |

In this experiment, photodynamic effect mediated by the compounds (except CEFO and CEFN) in different Examples of this disclosure on the murine mammary carcinoma 4T1 cells was investigated. The experimental procedures are carried out as follows. Cells in the logarithmic growth phase were harvested and seeded in a 24-well plate. After growing to a confluence of 70-80%, the cells were randomly divided into multiple photodynamic groups and multiple no-light control groups. The compounds (as shown in Table 8a) with a final concentration of 10 μg/mL were added to each group respectively in dark with 3 replicates for each group, so as to co-incubate the cells with the drug. Regarding the multiple photodynamic groups, the light irradiation was performed at a wavelength of 660 nm and the light intensity of 8 J/cm$^2$. After that, each group was digested, and were inoculated into a 96-well plate at 100 μL per well with 4 replicates for light treatment and no light treatment. 24 hours later, the 96-well plate was measured by MTT assay as follows. Each well was added with 20 μL of MTT (3-4,5-dimethylthiazol-2,5-diphenyltetrazolium bromide) solution in the dark and incubated for 4 hours. The supernatant was discarded, and the residue was dissolved with 150 μL of dimethyl sulfoxide for 15 min. After that, the 96-well plate was measured by a microplate reader for the absorbance (OD value). The relative cell viability of the murine mammary carcinoma 4T1 cells was calculated as follows according to the measured absorbance (OD value) in each group: relative cell viability=OD value of experimental group/OD value of control group*100%.

(3) Human Hepatocellular Carcinoma Huh-7 Cells

TABLE 9

Effects of light intensity and concentration of CEFN, CEFO, Ce6 and HPPH on cell viability (%) of human hepatocellular carcinoma huh-7 cells

|  | 1 μg/mL | 2 μg/mL | 5 μg/mL | 10 μg/mL |
|---|---|---|---|---|
| Blank group | 107 ± 3 | 105 ± 3 | 102 ± 3 | 103 ± 3 |
| Compound CEFN | 97 ± 2 | 95 ± 3 | 93 ± 3 | 93 ± 1 |
| Compound CEFN + 2 J/cm$^2$ | 101 ± 3 | 87 ± 2 | 61 ± 2 | 50 ± 2 |
| Compound CEFN + 4 J/cm$^2$ | 78 ± 3 | 68 ± 2 | 55 ± 3 | 12 ± 3 |
| Compound CEFN + 8 J/cm$^2$ | 90 ± 3 | 64 ± 3 | 47 ± 2 | 9 ± 2 |
| Compound CEFO | 99 ± 2 | 99 ± 2 | 97 ± 3 | 93 ± 4 |
| Compound CEFO + 2 J/cm$^2$ | 63 ± 3 | 58 ± 1 | 39 ± 2 | 25 ± 2 |
| Compound CEFO + 4 J/cm$^2$ | 60 ± 3 | 53 ± 3 | 24 ± 2 | 9 ± 1 |
| Compound CEFO + 8 J/cm$^2$ | 53 ± 3 | 30 ± 2 | 27 ± 1 | 7 ± 1 |
| Ce6 | 96 ± 1 | 94 ± 2 | 90 ± 2 | 87 ± 2 |
| Ce6 + 8 J/cm$^2$ | 42 ± 3 | 37 ± 3 | 37 ± 2 | 32 ± 3 |
| HPPH | 102 ± 4 | 98 ± 2 | 97 ± 1 | 101 ± 4 |
| HPPH + 8 J/cm$^2$ | 68 ± 3 | 37 ± 3 | 26 ± 2 | 12 ± 2 |

As shown from the data in the above tables, when a drug is used alone without performing photodynamic treatment, the compound Ce6 is toxic to the cells. Nevertheless, the CEFN and CEFO of this disclosure owns satisfactory cell compatibility, which will not lower the cell viability. It illustrates that the CEFN and CEFO of this disclosure has good safety in use. At the light intensity of 2-8 J/cm$^2$, the CEFN and CEFO enable to cause an effective lethal effect on human cervical cancer cell-Hela cells, human hepatocellular carcinoma huh-7 cells and murine mammary carcinoma 4T1 cells, which significantly lowers the cell viability, and is distinctly superior to that of the chlorin Ce6 drug and HPPH. Especially, when the concentration is higher than 5 μg/mL and the light intensity is 8 J/cm$^2$, the lethal effect is significantly beneficial, which demonstrates that the compound of this disclosure can be employed in photodynamic therapy of tumors.

Experimental Example 3 Antitumor Activity of Compounds of this Disclosure as Photosensitizers and Sonosensitizers on Tumor-Bearing Mice The murine mammary carcinoma cells (4T1 line) were subjected to adherent culture. After growing to a confluence of 70%-80%, the cells in the culture flask were routinely digested, centrifuged and counted, and then resuspended with 0.85% normal saline to a density of 1×10$^7$ cells/mL. The cell suspension was injected into the left lateral middle axillary subcutaneous part of Kunming mice Bal b/c healthy mice (female, aged 6-8 weeks) at 0.1 mL/mouse. When the tumor diameter, which was observed every other day, reached 0.6-0.8 cm, the mice with well-growing tumors and no ulcers on the epidermis were selected for grouped treatment.

1 Antitumor Activity of Compounds of this Disclosure as Photosensitizers on Tumor-Bearing Mice (1) Mice with similar body weight and uniform tumor size are selected and randomly divided into 7 groups with 6 mice for each group. After inoculation for 48 h, the mice were subjected to drug administration separately from the tail vein by group.

Blank group (PBS);
Positive control group with low-dose 2-(1-hexyloxy-ethyl)-2-devinyl pyropheophorbide-a (HPPH) (0.2 mg/kg);
Positive control group with high-dose HPPH (0.4 mg/kg);
low-dose CEFO group (0.2 mg/kg);
high-dose CEFO group (0.4 mg/kg);
low-dose CEFN group (0.2 mg/kg);
high-dose CEFN group (0.4 mg/kg).

6 h after the drug administration, the mice were fixed to expose the tumor growth site. Light irradiation was performed for 8 min, using PDT-660 photodynamic therapy equipment at a laser wavelength of 660 nm and a light dose of 75 Joule/cm$^2$. Then both of the mice growth and tumor growth are observed continuously. 7 days after photodynamic therapy, the animals were sacrificed. The tumor was stripped and weighed, and the body weight was recorded. The results are shown in Table 10.

TABLE 10

Inhibitory effect of PDT on murine mammary carcinoma 4T1 cells and effect of PDT on mice body weight

| Group | Drug concentration (mg/kg) | Tumor weight (average ± SD, g) | Inhibitory rate (average ± SD, %) | Body weight At the begining | Body weight At the end |
|---|---|---|---|---|---|
| PBS | 0 | 0.162 ± 0.013 | — | 20.6 ± 0.3 | 21.7 ± 0.3 |
| HPPH | 0.2 | 0.045 ± 0.006 | 72.2 ± 3.5 | 20.5 ± 0.4 | 21.6 ± 0.4 |
|  | 0.4 | 0.017 ± 0.004 | 89.5 ± 2.5 | 20.7 ± 0.3 | 21.8 ± 0.2 |
| CEFN | 0.2 | 0.051 ± 0.003 | 68.5 ± 1.7 | 20.6 ± 0.6 | 21.7 ± 0.5 |
|  | 0.4 | 0.028 ± 0.006 | 82.7 ± 3.7 | 20.5 ± 0.4 | 21.6 ± 0.5 |
| CEFO | 0.2 | 0.021 ± 0.005 | 87.0 ± 3.1 | 20.4 ± 0.3 | 21.5 ± 0.3 |
|  | 0.4 | 0.004 ± 0.001 | 97.5 ± 0.4 | 20.7 ± 0.4 | 21.8 ± 0.4 |

(2) Mice with similar body weight and uniform tumor size are selected and randomly divided into 4 groups with 6 mice for each group. After inoculation of 4T1 cells and the tumor volume grows to 50~80 mm$^3$, the mice were subjected to a first drug administration from the tail vein by group.

Blank group (PBS).
Positive control group (HPPH of 0.25 mg/kg).
CEFN group (0.25 mg/kg).
CEFO group (0.25 mg/kg).

6 h after the drug administration, the mice were fixed to expose the tumor growth site. As a first PDT treatment, light irradiation was performed for 8 min, using PDT-660 photodynamic therapy equipment at the laser wavelength of 660 nm and the light dose of 150 Joule/cm². One week later, the second PDT treatment (the dosage and lighting conditions were the same as those of the first PDT treatment) was performed. The mice were sacrificed 14 days after the treatment. The tumor was removed, weighed and recorded. The results are shown in Table 11.

TABLE 11

Inhibitory effects of two PDT treatments on murine mammary carcinoma 4T1 cells and effect of two PDT treatments on mice body weight

| Group | Drug concentration (mg/kg) | Tumor weight (average ± SD, g) | Inhibitory rate (average ± SD, %) | Body weight At the beginning | At the end |
|---|---|---|---|---|---|
| PBS | 0 | 0.949 ± 0.165 | | 20.4 ± 0.3 | 22.3 ± 0.3 |
| HPPH | 0.25 | 0.088 ± 0.020 | 90.7 ± 2.1 | 20.5 ± 0.4 | 22.5 ± 0.2 |
| CEFN | 0.25 | 0.132 ± 0.032 | 86.1 ± 3.5 | 20.3 ± 0.3 | 22.4 ± 0.4 |
| CEFO | 0.25 | 0.029 ± 0.028 | 96.9 ± 3.1 | 20.2 ± 0.2 | 22.2 ± 0.5 |

2. Antitumor Activity of the Compounds of this Disclosure as Sonosensitizers Against Tumor-Bearing Mice Mice with similar body weight and uniform tumor size are selected and randomly divided into 6 groups with 6 mice for each group. 48 h after inoculation, the mice were subjected to drug administration separately from the tail vein by group.

Blank group (PBS).
Positive control group (Ce6 of 5 mg/kg).
CEFO with low dose group (CEFO of 2.5 mg/kg).
CEFO with high dose group (CEFO of 5.0 mg/kg).
CEFN with low dose group (CEFN of 2.5 mg/kg).
CEFN with high dose group (CEFN of 5.0 mg/kg). 6 h after drug administration, each group of mice was anesthetized by intraperitoneal injection with 0.2 mL of 1% pentobarbital sodium. Then the mice were fixed to allow the tumor growth site exposed. The SDT group was treated using an ultrasonic therapeutic apparatus at an impulse waveform of 1.0 MHz and power of 3.0 W/cm² for 3 min. 7 days after SDT, the animals were sacrificed. The tumor was stripped and weighed, and the body weight was recorded. The results are shown in Table 12.

TABLE 12

Inhibitory effect of SDT on murine mammary carcinoma 4T1 cells and effect of SDT on mice body weight

| Group | Drug concentration (mg/kg) | Tumor weight (average ± SD, g) | Inhibitory rate (average ± SD, %) | Body weight At the beginning | At the end |
|---|---|---|---|---|---|
| PBS | 0 | 0.171 ± 0.011 | | 20.3 ± 0.4 | 21.4 ± 0.5 |
| Ce6 | 5 | 0.080 ± 0.005 | 53.3 ± 2.8 | 20.5 ± 0.4 | 21.4 ± 0.5 |
| CEFN | 2.5 | 0.099 ± 0.007 | 42.1 ± 4.2 | 20.5 ± 0.3 | 21.6 ± 0.2 |
|  | 5 | 0.057 ± 0.005 | 66.7 ± 3.0 | 20.3 ± 0.2 | 21.3 ± 0.3 |
| CEFO | 2.5 | 0.061 ± 0.007 | 64.3 ± 4.3 | 20.4 ± 0.3 | 21.4 ± 0.3 |
|  | 5 | 0.027 ± 0.004 | 84.2 ± 2.9 | 20.2 ± 0.2 | 21.3 ± 0.2 |

As indicated in the above test results, when the compound of this disclosure is employed as a photosensitizer in photodynamic therapy of tumors or as a sonosensitizer in sonodynamic therapy of tumors, the reduction of the body weight is unobvious, such that they are safe. At the same time, when employed as photosensitizers for photodynamic therapy or as sonosensitizers for sonodynamic therapy of tumors, the compound of this disclosure enables to significantly inhibit tumor growth and have good therapeutical effects. The therapeutical effect of the CEFO is superior to that of the CEFN. In all, the compounds of this disclosure can be used as photosensitizers for photodynamic therapy or sonosensitizers of sonodynamic therapy.

The above experimental results demonstrate that the compounds of this disclosure have good therapeutical effects when used as photosensitizers for photodynamic therapy or as sonosensitizers for sonodynamic therapy of tumors, and thus the compounds of the disclosure can be employed in the preparation of drugs for the treatment of tumors. At the same time, the compound has good safety and mild toxic and side effects, allowing for brilliant application prospects.

What is claimed is:

1. A compound of formula (I), or a salt, a stereoisomer, a hydrate, a solvate or a prodrug thereof:

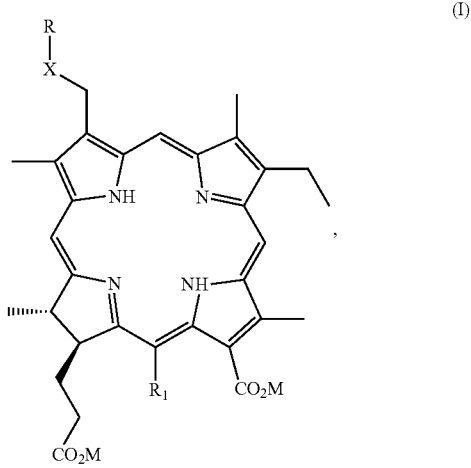

(I)

wherein R is selected from the group consisting of substituted and unsubstituted $C_{1-15}$ alkyl, substituted and unsubstituted $C_{2-15}$ alkenyl, substituted and unsubstituted $C_{2-15}$ alkynyl, substituted and unsubstituted $C_{1-15}$ acyl, substituted and unsubstituted 3-8 membered cycloalkyl, substituted and unsubstituted 5-10 membered heteroaryl, substituted and unsubstituted 5-15 membered heteroaralkyl, substituted and unsubstituted 6-15 membered aralkyl and substituted and unsubstituted 6-14 aryl; wherein the substituted $C_{1-15}$ alkyl, substituted $C_{2-15}$ alkenyl, substituted $C_{2-15}$ alkynyl, substituted $C_{1-15}$ acyl, substituted 3-8 membered cycloalkyl, substituted 5-10 membered heteroaryl, substituted 5-15 membered heteroaralkyl, substituted 6-15 membered aralkyl and substituted 6-14 aryl comprises one or more substituents independently selected from the group consisting of halogen, hydroxyl, amino, sulfhydryl, 3-8 membered cycloalkyl, 5-8 membered heteroaryl, 6-10 aryl, $C_{1-15}$ alkyl, $C_{2-15}$ alkenyl, $C_{2-15}$ alkynyl and $C_{1-15}$ acyl;

$R_1$ is hydrogen, methyl or carboxyl group;

X is O or NH; and

M is H, an alkali metal ion or $NH_4^+$.

2. The compound of claim 1, or a salt, a stereoisomer, a hydrate, a solvate or a prodrug thereof, wherein R is a $C_{1-12}$ alkyl; $R_1$ is hydrogen or methyl.

3. The compound of claim 1, or a salt, a stereoisomer, a hydrate, a solvate or a prodrug thereof, wherein the compound is represented by formula (II):

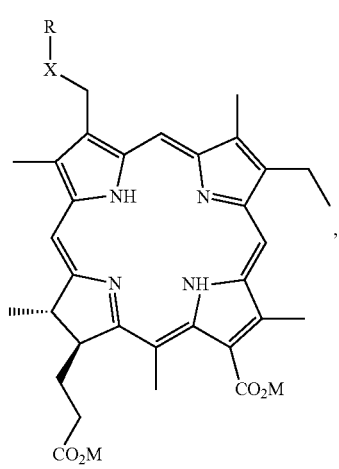

(II)

wherein R is a $C_{1-12}$ alkyl.

4. The compound of claim 3, or a salt, a stereoisomer, a hydrate, a solvate or a prodrug thereof, wherein the compound is represented by formula (II-1):

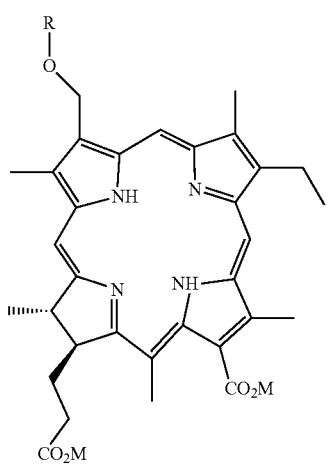

(II-1)

or by formula (II-2):

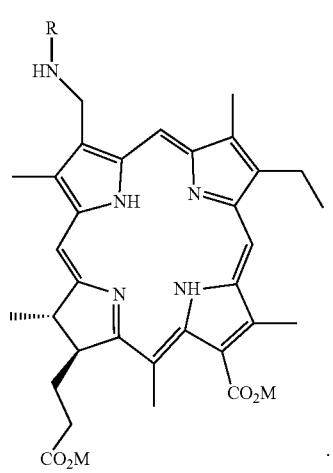

(II-2)

5. The compound of claim 4, or a salt, a stereoisomer, a hydrate, a solvate or a prodrug thereof, wherein the compound is represented by formula (III-1):

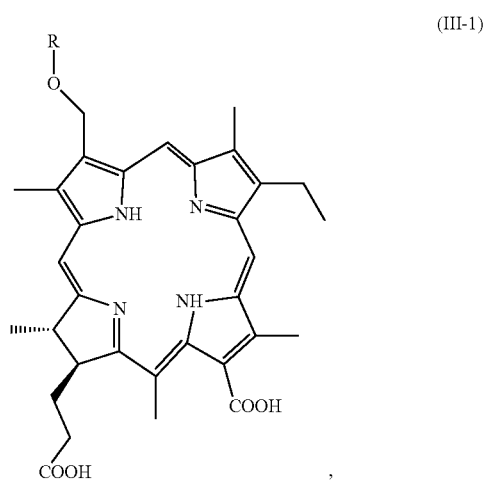

(III-1)

or by formula (III-2):

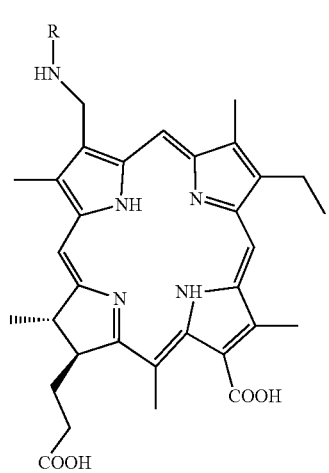

(III-2)

or by formula (III-3):

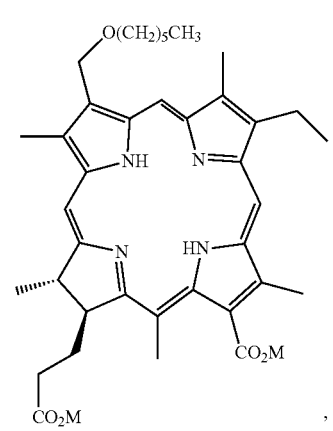

(III-3)

or by formula (III-4):
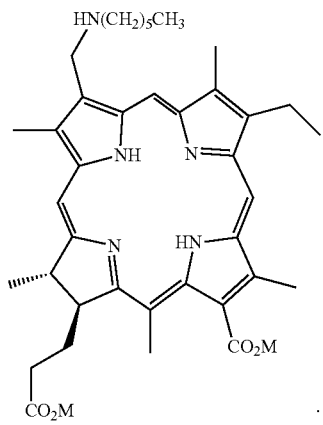
(III-4)
6. The compound of claim 1, or a salt, a stereoisomer, a hydrate, a solvate or a prodrug thereof, wherein the alkali metal ion is Na⁺ or K⁺.
7. The compound of claim 1, or a salt, a stereoisomer, a hydrate, a solvate or a prodrug thereof, wherein the compound is selected from the group consisting of:
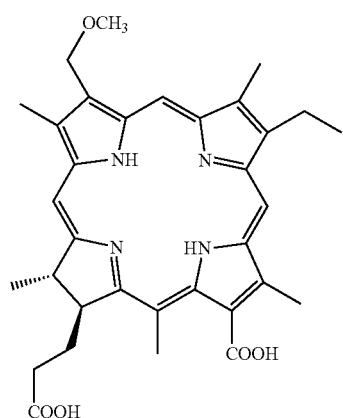
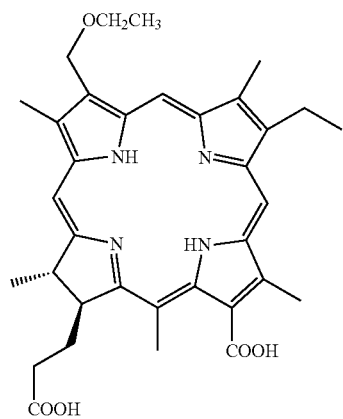
-continued
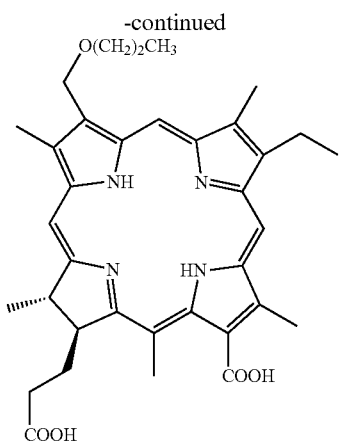
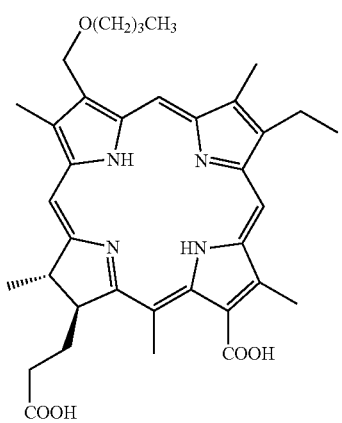
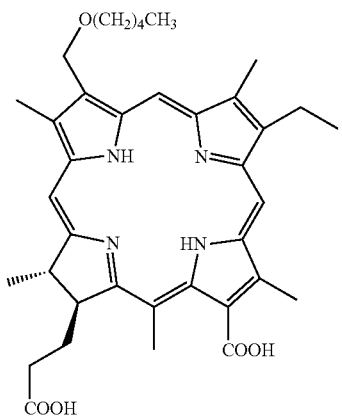
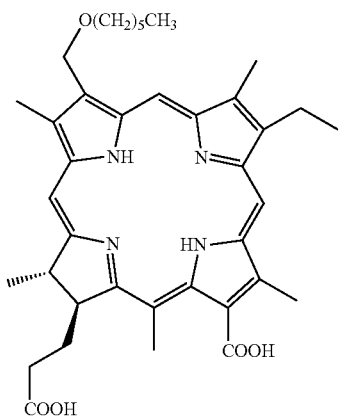

57
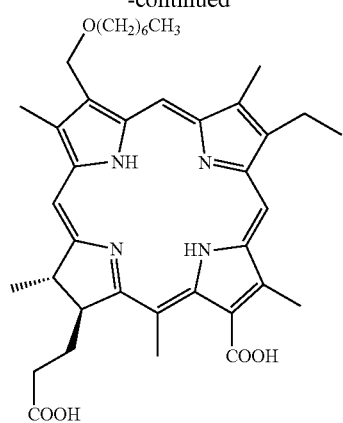
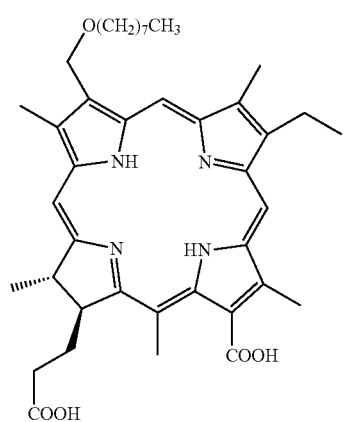
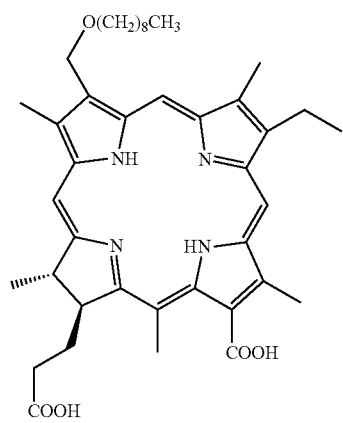
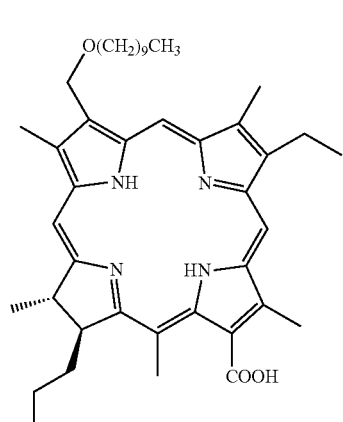
58
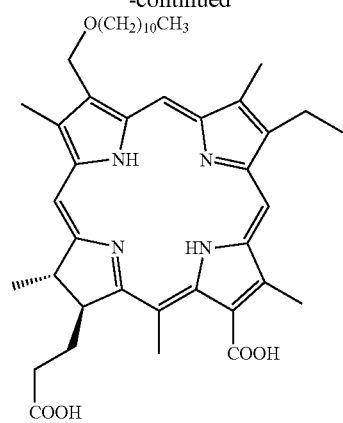
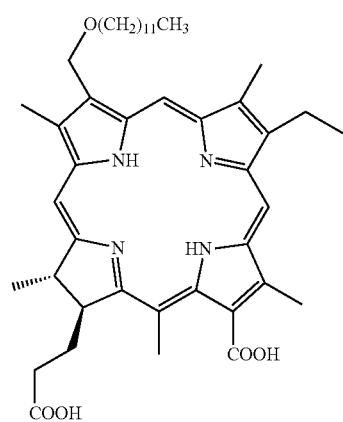
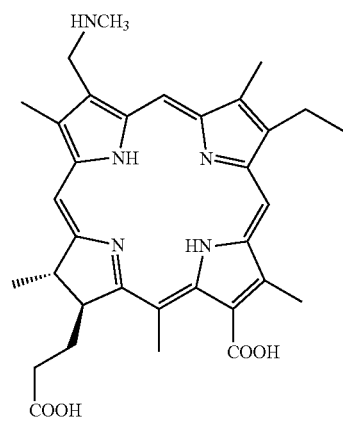
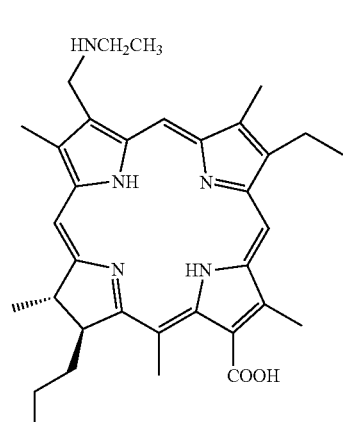

-continued
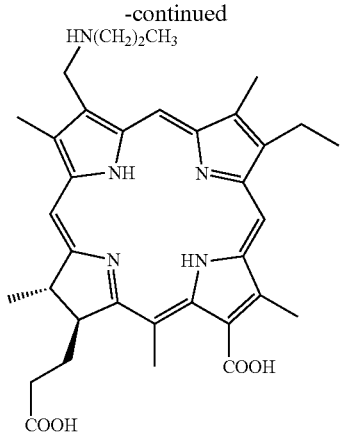
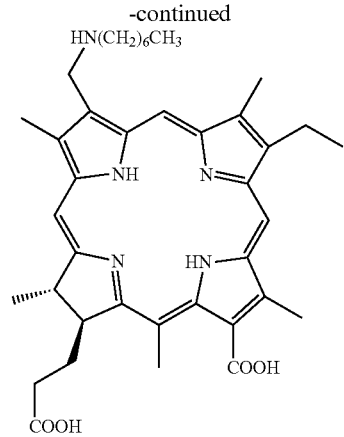
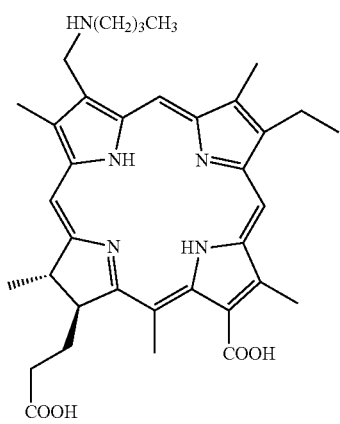
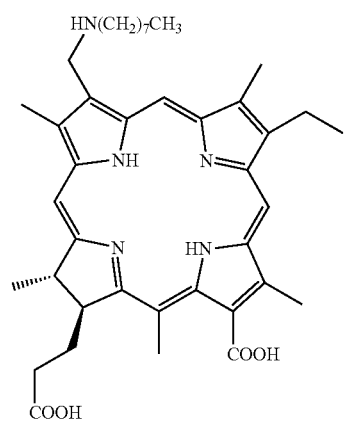
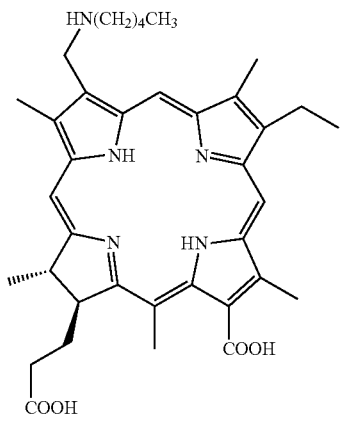
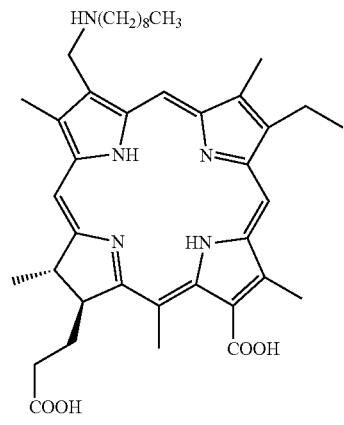
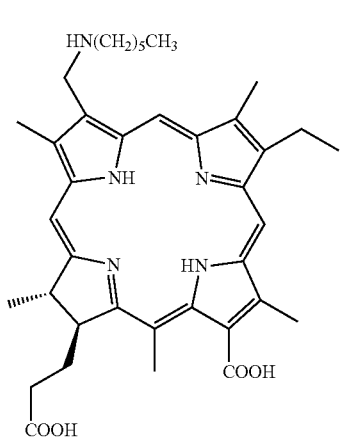
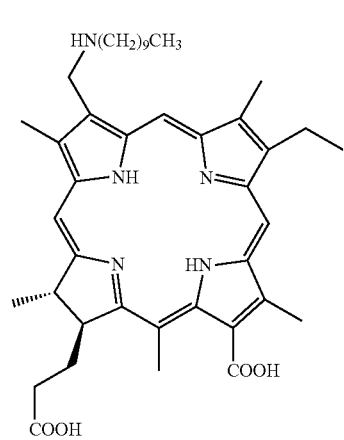

61
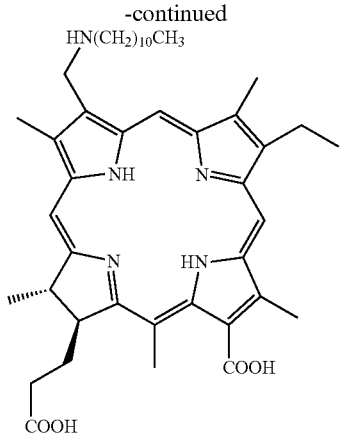
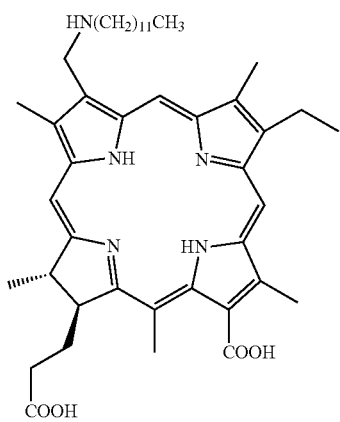
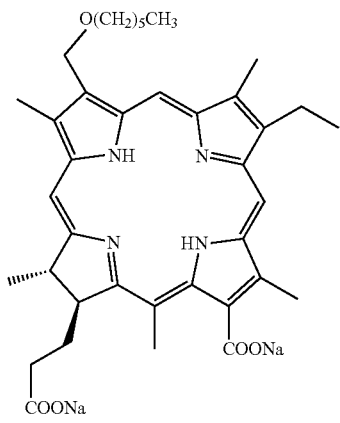
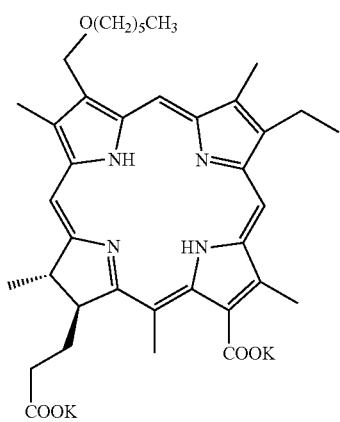
62
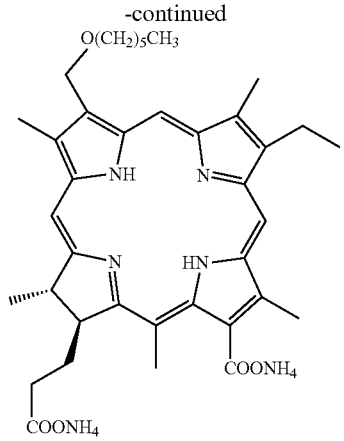
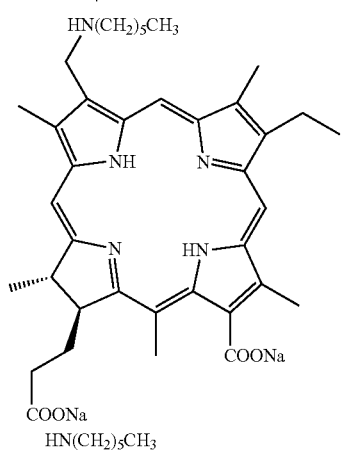
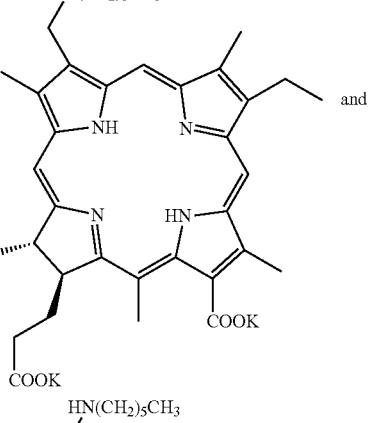
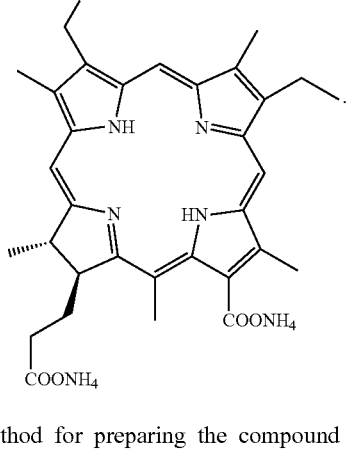
and
8. A method for preparing the compound of claim 3, comprising:

subjecting chlorin e4 to alkylation with (trimethylsilyl) diazomethane to produce chlorin e4 dimethyl ester;

reacting the chlorin e4 dimethyl ester with $NaIO_4$ in an aqueous solution containing $K_2OsO4$ and N-methyl-morpholine N-oxide (NMMO) to produce 3-formyl-3-devinyl-chlorin e4 dimethyl ester;

reacting the 3-formyl-3-devinyl-chlorin e4 dimethyl ester with t-$BuNH_2BH_3$ to produce 3-hydroxymethyl-3-devinyl-chlorin e4 dimethyl ester;

reacting the 3-hydroxymethyl-3-devinyl-chlorin e4 dimethyl ester with RONa in $SOCl_2$ to produce compound (IV); subjecting the compound (IV) to reaction in the presence of LiOH in methanol under reflux followed by pH adjustment with an acid to produce compound (III-1); and reacting the compound (III-1) with an alkali metal hydroxide or ammonium hydroxide to produce compound (II-1), as shown in the following reaction route:

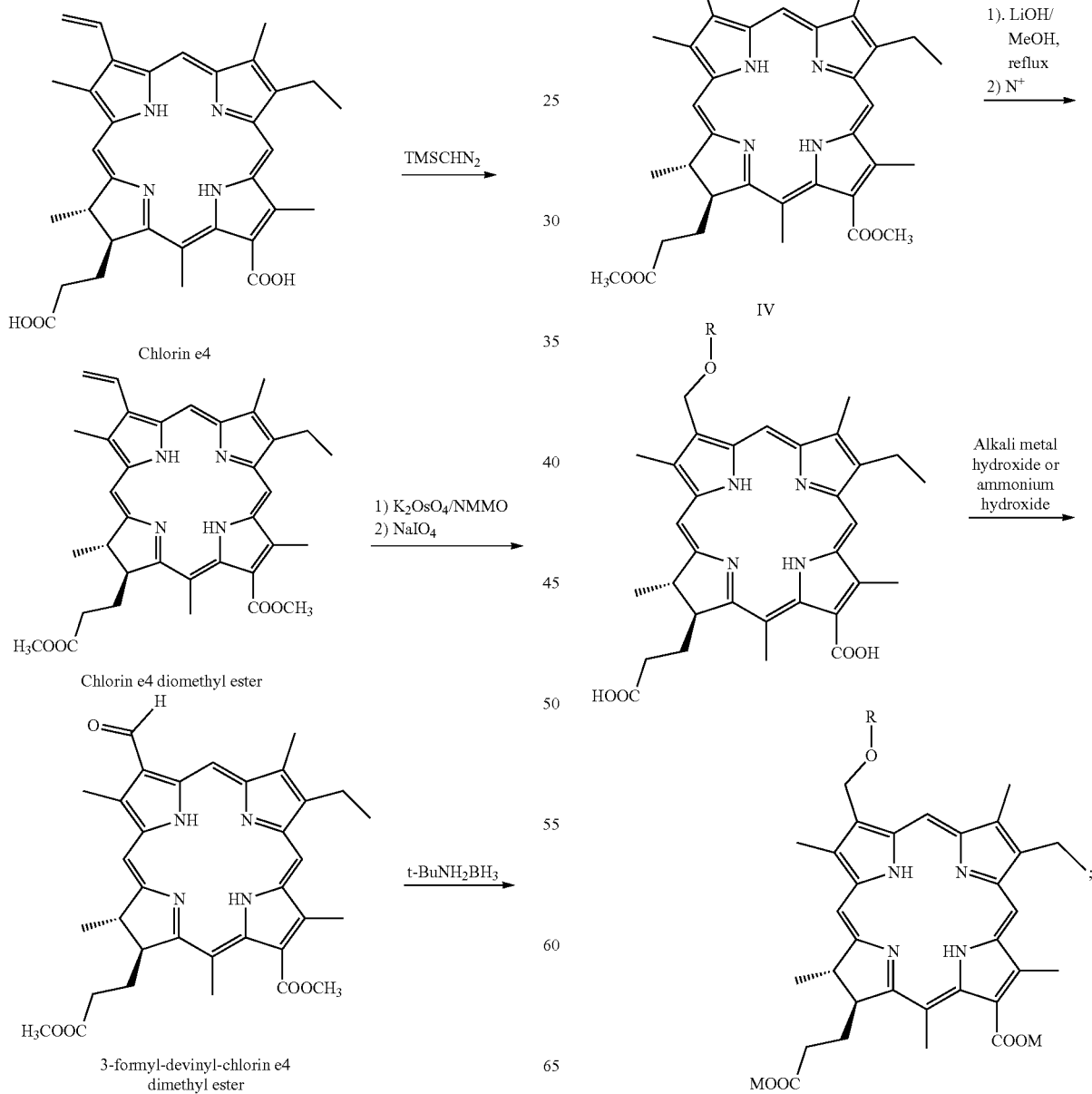

the method comprising:

reacting chlorin e4 with NaIO$_4$ in an aqueous solution containing K$_2$OsO4 and NMMO to produce 3-formyl chlorin-3-devinyl-e4;

reacting the 3-formyl chlorin-3-devinyl-e4 with NH$_2$R followed by reaction with NaBH4 in an ice bath to produce compound (III-2); and reacting the compound (III-2) with an alkali metal hydroxide or ammonium hydroxide to produce compound (II-2), as shown in the following reaction route:

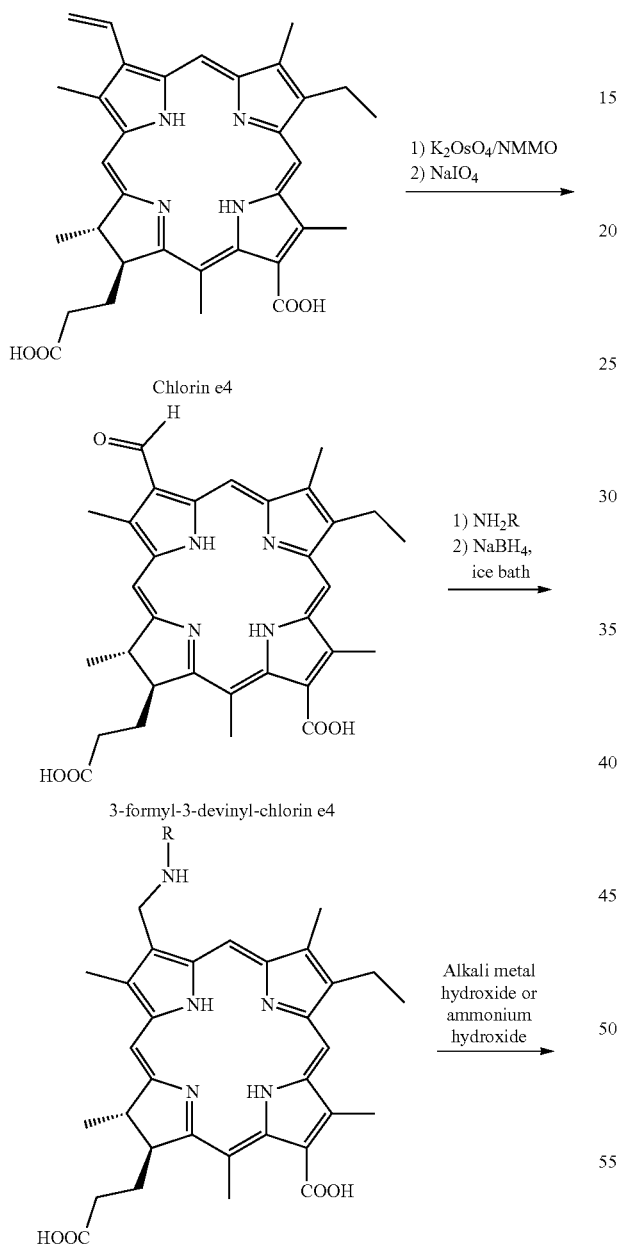

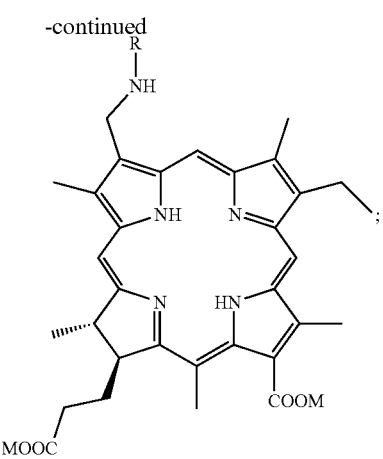

wherein R is a C$_{1-12}$ alkyl; and

M is H, an alkali metal ion or NH$_4^+$.

9. A method for therapeutically treating a disease in a subject in need thereof, comprising:

administering to the subject an effective amount of the compound of claim 1, or a salt, a stereoisomer, a hydrate, a solvate or prodrug thereof;

wherein the disease is a malignant tumor, a wherein the malignant tumor is a solid tumor selected from the group consisting of cervical cancer, liver cancer and breast cancer.

10. A drug, comprising:

the compound of claim 1, or a salt, a stereoisomer, a hydrate, a solvate or a prodrug thereof as an active ingredient; and a pharmaceutically acceptable excipient or auxiliary ingredient.

11. A pharmaceutical composition, comprising:

the compound of claim 1, a salt, a stereoisomer, a hydrate, a solvate or a prodrug thereof; and one or more pharmaceutically acceptable excipients.

12. A medicine box, comprising:

the compound of claim 1, a salt, a stereoisomer, a hydrate, a solvate or a prodrug thereof.

* * * * *